United States Patent
Hasui et al.

(10) Patent No.: US 8,652,522 B2
(45) Date of Patent: Feb. 18, 2014

(54) PHARMACEUTICAL COMPOSITION OF AN IONTOPHORESIS

(75) Inventors: Akihiro Hasui, Higashikagawa (JP); Takamitsu Miyagi, Sodegaura (JP)

(73) Assignee: Teikoku Seiyaku Co., Ltd., Kagawa (JP)

( * ) Notice: Subject to any disclaimer, the term of this patent is extended or adjusted under 35 U.S.C. 154(b) by 17 days.

(21) Appl. No.: 13/388,295

(22) PCT Filed: Jul. 28, 2010

(86) PCT No.: PCT/JP2010/004779
§ 371 (c)(1),
(2), (4) Date: Mar. 14, 2012

(87) PCT Pub. No.: WO2011/013359
PCT Pub. Date: Feb. 3, 2011

(65) Prior Publication Data
US 2012/0165782 A1    Jun. 28, 2012

(30) Foreign Application Priority Data
Jul. 31, 2009 (JP) .................. 2009-179895

(51) Int. Cl.
*A61K 9/14* (2006.01)
*A61N 1/30* (2006.01)

(52) U.S. Cl.
USPC .......................................... 424/488; 604/20

(58) Field of Classification Search
None
See application file for complete search history.

(56) References Cited

U.S. PATENT DOCUMENTS

2008/0188791 A1 * 8/2008 DiFiore et al. ............... 604/20
2011/0281834 A1 * 11/2011 Friden et al. .................. 514/174

FOREIGN PATENT DOCUMENTS

| EP | 0 900 576 | * | 3/1999 | ............... A61N 1/30 |
|---|---|---|---|---|
| EP | 0 900 576 A1 | | 3/1999 | |
| EP | 1 547 579 | * | 6/2005 | ............... A61K 9/00 |
| JP | 9248344 A | | 9/1997 | |
| WO | WO 2004/019902 | * | 3/2001 | ........... A61K 31/573 |
| WO | WO 2004/199902 | * | 8/2003 | ........... A61K 31/573 |
| WO | WO-2004019902 A1 | | 3/2004 | |
| WO | WO 2005/021008 | * | 3/2005 | ........... A61K 31/573 |
| WO | WO-2005021008 A1 | | 3/2005 | |

OTHER PUBLICATIONS

Kamath et al. "Elecrophoretic Evaluation of Mobility of Drugs Suitable for Iontophoresis". (Meth Find Exp Clin Pharmacol 1995 17(4): 227-232.*
Glass, J.M., et al., "The Quantity and Distribution of Radiolabeled Dexamethasone Delivered to Tissue by Iontophoresis," International Journal of Dermatology, vol. 19, pp. 519-525, (Nov. 1980).
Kamath, S.S., et al., "Electrophoretic Evaluation of the Mobility of Drugs Suitable for Iontophoresis," Meth. Find. Exp. Clin. Phermacol., vol. 17, No. 4, pp. 227-232, (1995).
Office Action issued Dec. 5, 2012, in Chinese Patent Application No. 20080033961.2.

* cited by examiner

*Primary Examiner* — Robert A Wax
*Assistant Examiner* — Danah Al-Awadi
(74) *Attorney, Agent, or Firm* — Birch, Stewart, Kolasch & Birch, LLP

(57) ABSTRACT

It is an object of the present inventions to produce a pharmaceutical composition for the iontophoresis wherein a drug stability is excellent, and it is easy to blend and fill up when manufactured and it is possible to manufacture at low cost. A pharmaceutical composition for an iontophoresis according to the present invention, is characterized in that the composition contains a nonionic synthetic polymer, betamethasone sodium phosphate and solvent. Furthermore, in a preferred embodiment of a pharmaceutical composition for an iontophoresis according to the present invention, the composition is characterized in that the nonionic synthetic polymer is polyvinyl alcohol (PVA). Furthermore, in a preferred embodiment of a pharmaceutical composition for an iontophoresis according to the present invention, the composition is characterized in that the mixing amount of the polyvinyl alcohol (PVA) is 0.5 to 30.0 percent by weight.

12 Claims, 8 Drawing Sheets segment No.®

BAS      BAS + segment      segment

PHARMACEUTICAL COMPOSITION OF AN IONTOPHORESIS This application is the National Phase under 35 U.S.C. §371 of International Application No. PCT/JP2010/004779 filed on Jul. 28, 2010, which claims priority under 35 U.S.C. §119(a)-(d) of Application No. 2009-179895 filed in Japan on Jul. 31, 2009.

TECHNICAL FIELD

The present invention relates to a pharmaceutical composition for an iontophoresis suitable for use in an application through a percutaneous route and a transmucosal route.

BACKGROUND ART

The iontophoresis is a method of delivering into a living organism a component such as an ionic medical agent useful for a living organism by using, what is called, an electrophoresis. This is also called as an ion transfer therapy, or an iontophoresis therapy, and is mainly used for a systemic drug administration.

The iontophoresis apparatus generally comprises a structure of electrode for an operation holding a pharmaceutical solution wherein the medicinal components (physiologically active substances) are dissociated into a positive ion or a negative ion (drug ion), a structure for a non-operation playing a rule for a counter electrode of the structure of electrode for an operation. The drug ions are administered into the living organism by adding the same polar voltage as the drug ions to the structure of electrode for an operation through the electric power unit under the condition that these both structures are in contact with the skin of the living organism (human or mammal). In rare cases, to both structures may be included the physiologically active substances, and the both electrodes may be a structure for an operation.

In the meantime, intra-articular administration of a water-soluble steroid is carried out as an injectable solution in the medical treatment of rheumatoid arthritis and arthrosis deformans etc. However, the mode of injection brings on pain when it is administered, so that an advanced technique by a medical doctor is required. Further, these are not absolutely a simple, safe, secure and highly available administering method in the medical drug field, since these medical treatment may lead to the infectious diseases from the site of administration.

In order to solve the above problems, it is known the dermal administration of dexamethasone sodium phosphate which is one of the water-soluble steroid by using a direct-current type of the iontophoresis (Nonpatent literature 1).

PRIOR ART DOCUMENT

[Nonpatent literature 1] International Journal of Dermatology. Vol. 19 (1990), pages 519-525 (Int. J. Dermatol. 19. (1990) 519-525)

DISCLOSURE OF INVENTION

Problems to be Resolved by the Invention

However, in the administration according to the above injectable solution, the administration must be carried out at time intervals, two weeks or more, since for example, the administration must be carried out in consideration of the conditions of the living body such as the side effects. Furthermore, these methods need to attend a hospital, and are not necessarily a simple and highly available administering method when asking for the therapeutic effect. Therefore, an effective administration method have been desired.

Furthermore, in the administration according to the above nonpatent literature, although it is based on the premise of the use of lidocaine which is a local anesthetic drug in order to block an electric stimulus or a pain, it has a problem that they are not necessarily a simple and safe administration method from a practical standpoint.

Moreover, although it is desired that the pharmaceutical composition applied for the iontophoresis has more long-term stability, under present circumstances, an attempt to the preparation of the pharmaceutical composition from the viewpoint of the above matter is almost never done.

Therefore, it is an object of the present inventions to produce a pharmaceutical composition for the iontophoresis wherein a drug stability is excellent, and it is easy to blend and fill up when manufactured and it is possible to manufacture at low cost.

Means of Solving the Problems

In order to accomplish the above objects, the present inventors made strenuous studies on a relationship between the water-soluble steroid and the long-term stability. As a result, the inventors discovered the present invention.

That is, a pharmaceutical composition for an iontophoresis according to the present invention, is characterized in that the composition contains a nonionic synthetic polymer, betamethasone sodium phosphate and solvent.

Furthermore, in a preferred embodiment of a pharmaceutical composition for an iontophoresis according to the present invention, the composition is characterized in that the nonionic synthetic polymer is polyvinyl alcohol (PVA).

Furthermore, in a preferred embodiment of a pharmaceutical composition for an iontophoresis according to the present invention, the composition is characterized in that the mixing amount of the polyvinyl alcohol (PVA) is 0.5 to 30.0 percent by weight.

Furthermore, in a preferred embodiment of a pharmaceutical composition for an iontophoresis according to the present invention, the composition is characterized in that the mixing amount of the polyvinyl alcohol (PVA) is less or equal to 20 percent by weight.

Furthermore, in a preferred embodiment of a pharmaceutical composition for an iontophoresis according to the present invention, the composition is characterized in that the mixing amount of betamethasone sodium phosphate is 1 to 12 percent by weight.

Furthermore, in a preferred embodiment of a pharmaceutical composition for an iontophoresis according to the present invention, the composition is characterized in that the mixing amount of betamethasone sodium phosphate is 1 to 4 percent by weight.

Furthermore, in a preferred embodiment of a pharmaceutical composition for an iontophoresis according to the present invention, the composition is characterized in that the solvent is at least one selected from the group comprising water, phosphate buffer solution.

Furthermore, in a preferred embodiment of a pharmaceutical composition for an iontophoresis according to the present invention, the composition is characterized in that the pH on the surface of the composition is in the range of 7 to 8.

Furthermore, in a preferred embodiment of a pharmaceutical composition for an iontophoresis according to the present invention, wherein the composition further contains ethylenediamine tetraacetic acid (EDTA).

Furthermore, in a preferred embodiment of a pharmaceutical composition for an iontophoresis according to the present invention, the composition is characterized in that the mixing amount of ethylenediamine tetraacetic acid (EDTA) is 0.05 to 0.15 percent by weight.

Furthermore, in a preferred embodiment of a pharmaceutical composition for an iontophoresis according to the present invention, the composition is characterized in that the concentration of phosphate buffer solution is 1 to 10 mM.

Furthermore, a drug product for an iontophoresis according to the present invention, is characterized by comprising the composition according to any one of claims 1 to 11, and an adhesive layer.

Furthermore, in a preferred embodiment of the drug product for an iontophoresis according to the present invention, the drug product is characterized in that the adhesive layer comprises at least one selected from the group comprising acrylic system, silicon system, synthetic rubber system and natural rubber system etc.

Furthermore, an administrating method using an iontophresis according to the present invention, is characterized in that betamethasone sodium phosphate is administered by using the pharmaceutical composition according to the present inventions.

Furthermore, in a preferred embodiment of an administrating method using an iontophresis according to the present invention, the method is characterized in that betamethasone sodium phosphate is transferred to an arthrosis through a percutaneous route by going through a perimysia from a supporting layer, and being zonary distributed to the inner side of a perimysia and a synovial membrane.

Furthermore, an method of treatment of rheumatoid arthritis, arthrosis deformans, tendinitis, tendovaginitis, peritendinitis according to the present invention is characterized in that at least one disorder selected from the group comprising rheumatoid arthritis, arthrosis deformans, tendinitis, tendovaginitis, peritendinitis (in this regard, however any disorder described in the above is limited to a noninfectious) is treated by administering betamethasone sodium phosphate according to the administrating method of the present inventions.

Effect of Invention

According to the present inventions, they have an advantageous effect that the residual ratio of the pharmaceutical composition become stable over the long term, and the stability of the drug product is excellent. Furthermore, according to the present invention, it has an advantageous effect that it is possible to attain the excellent drug effectiveness without no issue of taking off from the water etc., on the component in the prior art, because the unnecessary components are eliminated as much as possible and the minimum essential component is used.

MODE FOR CARRYING OUT THE INVENTION

Figure 1:
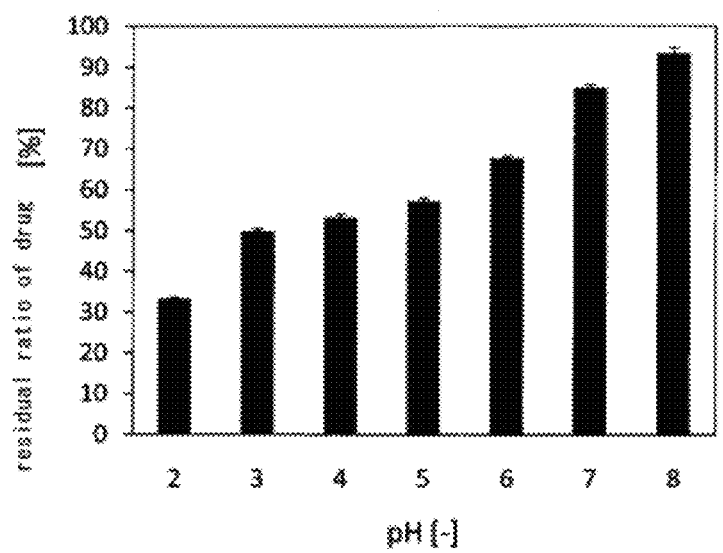
FIG. 1 gives a residual ratio of the chemical drug in various sorts of pH.

A pharmaceutical composition for an iontophoresis according to the present invention contains a nonionic synthetic polymer, betamethasone sodium phosphate and solvent. As a nonionic synthetic polymer used for the pharmaceutical composition for the iontophoresis of the present invention, it is not particularly limited as long as it is hydrophilic and a nonionic synthetic polymer, however, for example, mention may be made of synthetic polymers such as polyvinyl alcohol, polyvinyl formal, polyvinyl methyl ether, polyvinyl methacrylate, polyvinyl pyrrolidone, copolymer of polyvinyl pyrrolidone and vinyl acetate, polyethylene oxide, polypropylene oxide etc. From a view point that it is easy to manufacture, among them, polyvinyl alcohol, polyvinyl pyrrolidone, polyethylene oxide are preferable. These are used in one or more in appropriate combination.

The mixing amount of such nonionic synthetic polymer is preferably 0.5 to 30.0 percent by weight, in the pharmaceutical composition for an iontophoresis. In the case that the mixing amount become less of 0.5 percent by weight, a sufficient shape retention and an adherence may be not obtained. On the other hand, in the case that the mixing amount become greater than 30 percent by weight, a handleability and a filling property when manufactured may be reduced by increasing degree of viscosity. Furthermore, in a preferred embodiment of the pharmaceutical composition for an iontophoresis according to the present invention, the mixing amount of the polyvinyl alcohol (PVA) is less or equal to 20 percent by weight. This is because of the prevention of both a stringing caused by the nonionic synthetic polymer and a degradation of productivity caused by increasing the degree of viscosity. More preferably, it is less or equal to 16 percent by weight, furthermore preferably, it is 14 to 16 percent by weight.

Furthermore, in a preferred embodiment of a pharmaceutical composition for an iontophoresis according to the present invention, the mixing amount of betamethasone sodium phosphate is not particularly limited, however, from a viewpoint of an effect of enhancement of permeation by the electric field in the concentration of the drug product at a donor, it is 1 to 12 percent by weight, more preferably it is 1 to 4 percent by weight form a viewpoint of an efficiency of enhancement of permeation.

Furthermore, in a preferred embodiment of a pharmaceutical composition for an iontophoresis according to the present invention, the solvent is at least one selected from the group comprising water, phosphate buffer solution. The water blended in the pharmaceutical composition for the iontophoresis of the present invention is very important component on administration according to the iontophoresis from a viewpoint of the swelling of a horny layer of the skin, the moderation of stimulation, and a dissolution and a permeation of the administered chemical drug. The mixing amount of water for the total weight of the pharmaceutical composition for the iontophoresis is preferably 10 to 80 percent by weight, more preferably 30 to 60 percent by weight. In the case that the mixing amount is less than 10 percent by weight, the resolvability of the water-soluble chemical drug existing in the composition may be reduced to precipitate a crystal, the amount of the free water in the composition may be reduced to increase the diffusion resistance, as a result, and thereby reducing the absorbed amount of the chemical drug. On the other hand, in the case that the mixing amount is greater than 80 percent by weight, it become difficult to form a sufficient gel body, it gives the difficulty of the quality guarantee when the storage and the administration because a volatile of water become high.

In addition, a pH of on the surface of the pharmaceutical composition for the iontophoresis according to the present invention is not particularly limited. It depends on the stability of the chemical drug and the electrode for administering, and it may be varied. However, the pH of the composition is preferably in the range of 4 to 9, more preferably in the range of 7 to 8, from a viewpoint of the stability of the chemical drug, the stability for the skin and the gel property.

Furthermore, in the pharmaceutical composition for the iontophoresis of the present invention, the composition may further contain ethylenediamine tetraacetic acid (EDTA). The ethylenediamine tetraacetic acid (EDTA) makes it possible to control the hardening of the metal based chemical compound, and makes it possible to trap a metal ion, particularly $Ag^+$ with chelate, and thereby making a contribution to the stability of the chemical drug. The mixing amount of ethylenediamine tetraacetic acid (EDTA) is not particularly limited, however, from a viewpoint that it does not prevent the chemical drug from permeating through the skin, the mixing amount of ethylenediamine tetraacetic acid (EDTA) is preferably 0.05 to 0.15 percent by weight.

Furthermore, in a preferred embodiment of the pharmaceutical composition for the iontophoresis according to the present invention, from a viewpoint that it is possible to reduce a pH change of gel surface over long periods, and to prevent the competition of betamethasone sodium phosphate in the skin permeation when applying current, the concentration of phosphate buffer solution is 1 to 10 mM, and more preferably 1 to 5 mM.

Furthermore, a drug product for an iontophoresis according to the present invention comprises the pharmaceutical composition for the iontophoresis of the present invention described in the above and an adhesive layer. For example, the adhesive layer comprises at least one selected from the group comprising acrylic system, silicon system, synthetic rubber system and natural rubber system. The adhesive layer is preferably acrylic system.

Furthermore, in the pharmaceutical composition for the iontophoresis according to the present invention, in the scope which does not depart from the purpose of the present invention that provides a stable pharmaceutical composition being eliminated the negative effects caused by an additive with the use of minimum necessary component, the composition may contain a preservation agent, an antiseptic agent.

In the method of the pharmaceutical composition according to the present invention, into a proper vessel are added a solvent and a nonionic synthetic polymer, and stirred according to need. This is soused in the heated oil bath, and heated with agitating for 20 to 60 minutes, and cooled down under the room temperature with agitating according to need.

After it drop in temperature, to this is added the betamethasone sodium phosphate solution and added a purified water according to need, and stirred again to become uniform. By this means, the pharmaceutical composition according to the present invention may be obtained.

Next, an administrating method using an iontophresis of the present invention will be explained. An administrating method using an iontophresis of the present invention is characterized in that betamethasone sodium phosphate is administered by using the pharmaceutical composition according to the present inventions. The explanation of the pharmaceutical composition according to the present inventions may be quoted from the explanation as mentioned above.

In the administration, the above mentioned pharmaceutical composition of the present inventions may be applied on the electrode wherein an electrically conductive paste is preliminarily formed by printing out at the surface of application in the support medium, or after the pharmaceutical composition may be applied or filled up to a film carried out a delamination treatment once or into a molded cup, the composition may be transferred and clamped under the pressure to the electrode, and thereby it being possible to obtain the electrode for the iontophresis. The electrode obtained thus and the apparatus for the iontophresis according to the conventional means may be used to administer.

Furthermore, the present inventions make it possible to produce an iontophresis apparatus by using the above mentioned pharmaceutical composition of the present inventions wherein betamethasone sodium phosphate may be transferred to an arthrosis through a percutaneous route by going through a perimysia from a supporting layer, and being zonary distributed to the inner side of a perimysia and a synovial membrane.

Furthermore, the use of an method of administrating betamethasone sodium phosphate using the iontophresis of the present invention makes it possible to treat at least one disorder selected from the group comprising rheumatoid arthritis, arthrosis deformans, tendinitis, tendovaginitis, peritendinitis (in this regard, however any disorder described in the above is limited to a noninfectious).

Example 1

The present invention will be concretely explained in more detail with reference to Examples, but the invention is not intended to be interpreted as being limited to Examples.

<Manufacture Procedure (as a 100 g Scale)>

Into a separable beaker was added 15 g of PVA (polyvinyl alcohol) and added also a purified water (In the case that EDTA (ethylenediamine tetraacetic acid) is added, it was added in this time. Furthermore, in that case that the buffer solution is used, it is prepared by using the buffer solution instead of a purified water). The lid of the beaker was closed, a paddle for stirring was equipped. This was immersed in an oil bath at 120° C., and heated at 30 minutes with stirring. This was took out from the oil bath, and was cooled under the room temperature with stirring. When falling in temperature up to 60° C., betamethasone sodium phosphate solution was added and stirred to obtain a 3%. To this was added water to obtain 100 g of the mixture solution. This was stirred again to become uniform. After sufficient stirring, the mixture solution was absorbed by syringe. To the drug product prepared with the foam tape (made in 3M, closed cell foam tape, model number 9773) was dispensed about 1 g of the solution manufactured thus. This was kept in the freezer at −80° C., and freezed to accelerate gelatinization of PVA. After freezing this almost through the night, this was left at rest under the room temperature to unfreeze. This was singly divided into a packing material made of aluminum, and was added into an apparatus with constant temperature and humidity set at various temperature and thereby a stability test being carried out.

Example 2

Figure 2:
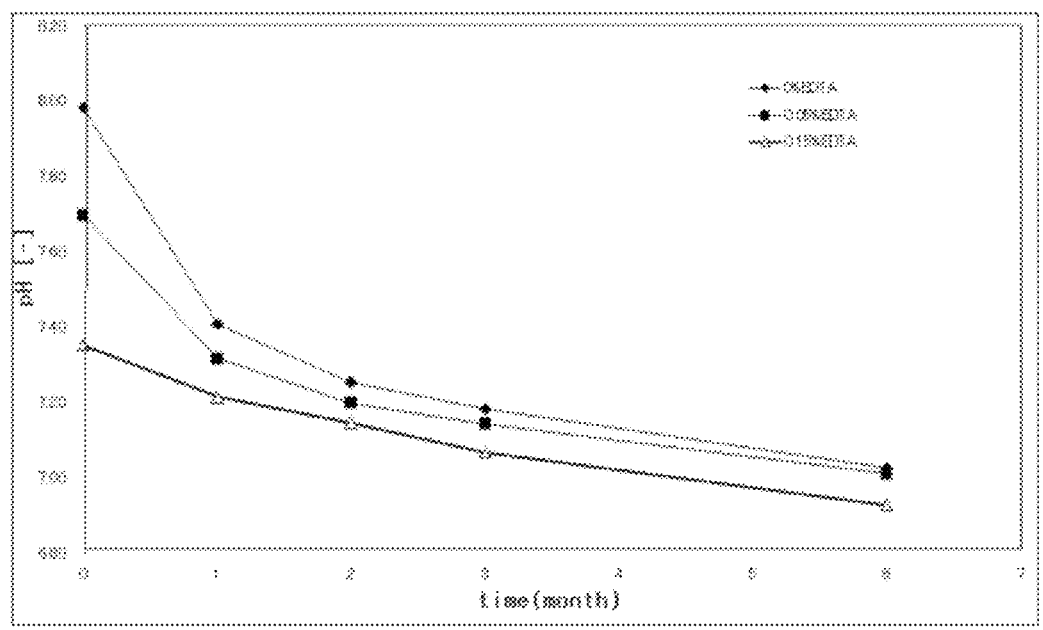
FIG. 2 gives a result in the case that the acceleration test at 40° C. was carried out on the pharmaceutical composition of an example of the present invention.

Next, as to the composition prepared according to the example 1, an acceleration test was carried out at 40° C., in the case that an amount of EDTA is varied. The stability of the chemical drug was examined by carrying out the pH measurement of the gel at this time. The table 1 and the FIG. 2 gives a result in the case that the acceleration test at 40° C. was carried out on the pharmaceutical composition of an example of the present invention. In the table 1, it gives a pH change after 1, 2, 3, 6 months in (a), (b) and (c), wherein (a) is in the case of 0% of EDTA, (b) is in the case of 0.05% of EDTA, and (c) is in the case of 0.15% of EDTA, respectively.

TABLE 1

| pH\month | 0 | 1 | 2 | 3 | 6 |
|---|---|---|---|---|---|
| (a)0 0% | | | | | |
| | 8.02 | 7.43 | 7.28 | 7.15 | 7.06 |
| | 8.01 | 7.41 | 7.24 | 7.19 | 7.01 |
| | 7.91 | 7.4 | 7.26 | 7.18 | 7.02 |
| | | 7.38 | 7.25 | 7.16 | 7.01 |
| | | | 7.23 | 7.2 | 7.02 |
| | | | | 7.2 | |
| average | 7.98 | 7.41 | 7.25 | 7.18 | 7.02 |
| S.D. | 0.06 | 0.02 | 0.02 | 0.02 | 0.02 |
| (b)0.05 0.05% | | | | | |
| | 7.73 | 7.29 | 7.24 | 7.14 | 7.03 |
| | 7.67 | 7.34 | 7.15 | 7.15 | 7.01 |
| | 7.69 | 7.34 | 7.2 | 7.14 | 7.01 |
| | | 7.31 | 7.2 | 7.14 | 7 |
| | | 7.29 | 7.2 | 7.14 | 6.99 |
| | | | 7.2 | | |
| average | 7.70 | 7.31 | 7.20 | 7.14 | 7.01 |
| S.D. | 0.03 | 0.03 | 0.03 | 0.00 | 0.01 |
| (c)0.15 0.15% | | | | | |
| | 7.37 | 7.23 | 7.17 | 7.08 | 6.93 |
| | 7.36 | 7.22 | 7.16 | 7.07 | 6.92 |
| | 7.32 | 7.22 | 7.13 | 7.06 | 6.95 |
| | | 7.18 | 7.14 | 7.06 | 6.9 |
| | | 7.21 | 7.12 | 7.06 | 6.93 |
| average | 7.35 | 7.21 | 7.14 | 7.07 | 6.93 |
| S.D. | 0.03 | 0.02 | 0.02 | 0.01 | 0.02 |

As a result, it is assumed that a pH is reduced with time, a stable drug formulation may be obtained if the reduction of this pH can be prevented.

Example 3

Figure 3:
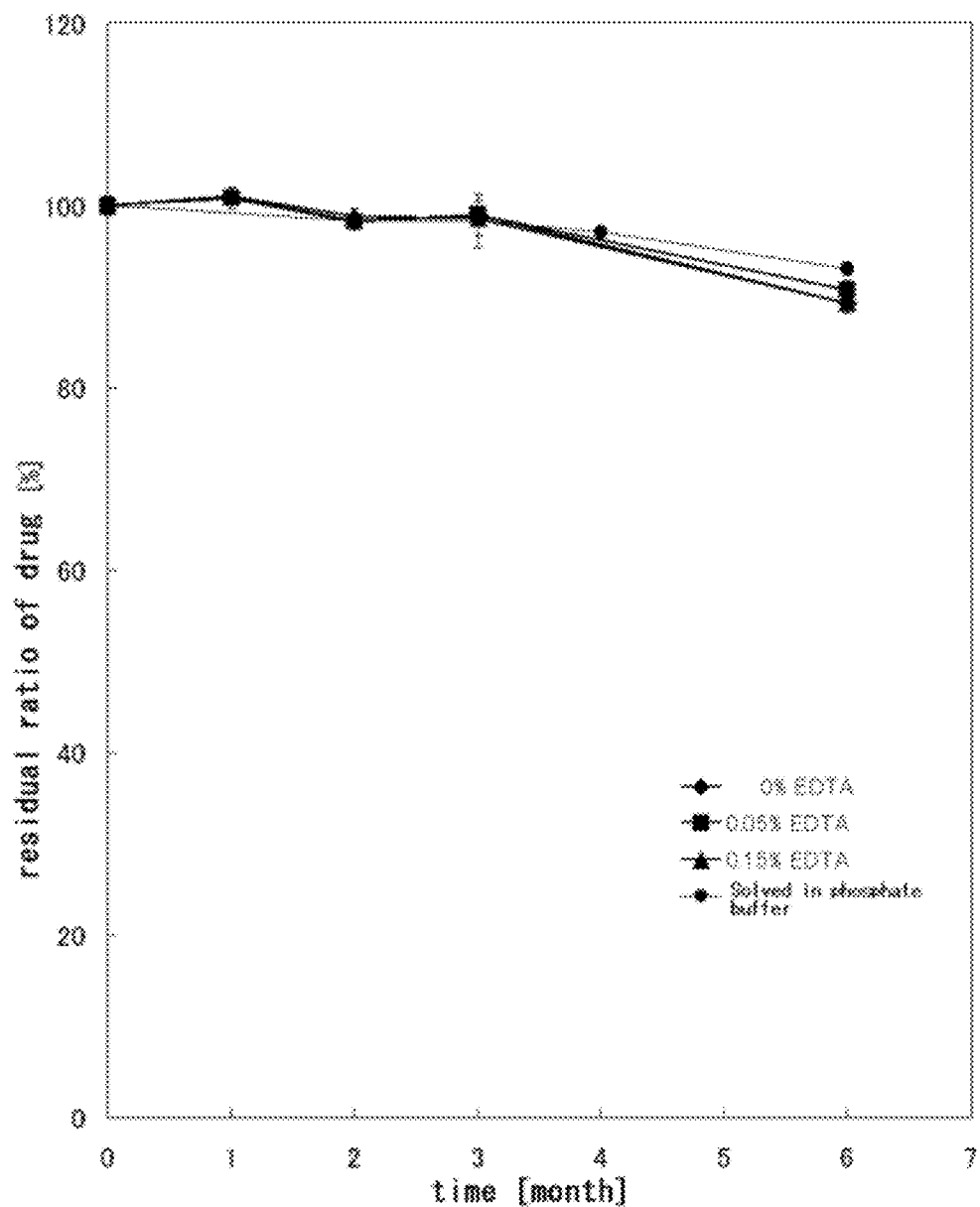
FIG. 3 gives a residual ratio of the chemical drug in the acceleration test at 40° C. of the gel drug product in the case of the addition of EDTA (ethylenediamine tetraacetic acid), or in the case of under the phosphate buffer solution (no addition of EDTA as to the acceleration test in 1 mM phosphate buffer solution)

Next. in the case that EDTA is added and in the case that phosphate buffer solution is used, a residual ratio of the chemical drug in an acceleration test at 40° C. was examined. The table 2 and the FIG. 3 give a residual ratio of the chemical drug in the acceleration test at 40° C. of the gel drug product in the case of the addition of EDTA (ethylenediamine tetraacetic acid), and in the case of under the phosphate buffer solution.

TABLE 2

| | Month | 0 | 1 | 2 | 3 | 6 |
|---|---|---|---|---|---|---|
| 0% EDTA | Mean | 100 | 100.94 | 98.28 | 98.99 | 89.27 |
| (formula by only water) | S.D. | 0 | 0.56 | 0.90 | 0.13 | 1.12 |
| 0.05% EDTA | Mean | 100 | 100.72 | 98.20 | 99.03 | 90.71 |
| | S.D. | 0 | 1.16 | 0.91 | 0.57 | 1.01 |
| 0.15% EDTA | Mean | 100 | 101.08 | 98.80 | 98.62 | 89.26 |
| | S.D. | 0 | 0.52 | 0.80 | 1.84 | 0.51 |
| 1 mM phosphate buffer 40° C. | Mean | 100 | 98.36 | 98.27 | 97.06 | 93.06 |
| | S.D. | 0.99 | 0.40 | 2.96 | 0.19 | 0.70 | n = 5 as to everything

As a result of this, it is recognized that as assumed in the example 3, the use of phosphate buffer solution etc., makes it possible to prevent the reduction of the pH, and consequently to suppress the reduction of a residual ratio of the chemical drug.

Example 4

Next, a pH change was examined in the case that the pharmaceutical composition was solved in water or gel etc. The table 3 gives pH change in the solution added a chemical drug. In the table, BSP means betamethasone sodium phosphate.

TABLE 3

| con. in solution | pH |
|---|---|
| 1% BSP, 0.05% EDTA | 7.36 |
| 1% BSP, 0.25% EDTA | 6.75 |
| 9% BSP, 0.05% EDTA | 7.83 |
| 9% BSP, 0.25% EDTA | 7.45 |

As a result of the table 3, it was revealed that a pH moves closer to alkari side if the chemical drug is added. Moreover, it was also revealed that a pH moves strongly closer to an alkari side if the concentration of the chemical drug is increased. On the other hand, it was revealed that EDTA makes it possible to incline a pH to an acid side.

Moreover, a pH change was also examined in the case that the pharmaceutical composition was solved in gel. The tables 4 and 5 give pH change in the surface of the gel added a chemical drug. The table 5 (a) gives an average value in the case that the pH in the surface of one gel is measured 7 to 8 times. The table 5 (b) gives a summary of the average value obtained in the table 5(a). In the table 5, Beta-P means betamethasone sodium phosphate.

TABLE 4

| con. of drug % (w/w) | 1 | 3 | 3 | 3 | 9 | 9 |
|---|---|---|---|---|---|---|
| con. of EDTA % (w/w) | 0.05 | 0 | 0.05 | 0.15 | 0 | 0.05 |
| pH of gel surface | 7.45 | 8.02 | 7.63 | 7.29 | 8.16 | 7.99 |

TABLE 5

(a)

|   | 1% Beta-P, 0.05% EDTA | 9% Beta-P | 9% Beta-P, 0.05% EDTA |
|---|---|---|---|
| 1 | 7.47 | 8.19 | 8.01 |
| 2 | 7.45 | 8.07 | 7.86 |
| 3 | 7.49 | 8.11 | 7.98 |
| 4 | 7.43 | 8.25 | 8.01 |
| 5 | 7.44 | 8.14 | 8 |
| 6 | 7.43 | 8.15 | 8.02 |
| 7 | 7.43 | 8.16 | 8.03 |
| 8 |  | 8.19 | 7.99 |
| Mean | 7.45 | 8.16 | 7.99 |
| SD | 0.02 | 0.05 | 0.05 |

(b) gel

| contents in gel | pH Mean | S.D. |
|---|---|---|
| 1% (w/w)Beta-P, 0.05% (w/w)EDTA | 7.45 | 0.02 |
| 9% (w/w)Beta-P | 8.16 | 0.05 |
| 9% (w/w)Beta-P, 0.05% (w/w)EDTA | 7.99 | 0.05 |

As a result of the tables 4 and 5, it was revealed that a pH in the surface of the gel is also inclined to an alkari side in the case of the addition of the chemical drug. Moreover, it was also revealed that a pH moves strongly closer to an alkari side if the concentration of the chemical drug is increased. On the other hand, it was revealed that EDTA makes it possible to incline a pH to an acid side. As a result of this, it was revealed that in the gel the same pattern as the solution may be obtained.

Example 5

Next, the stability of the chemical drug under the wide area of the buffer solution at pH 2 to 8 was examined. In more details, pH 2 to pH 8 were prepared by using a wide area of the buffer solution by Briton-Robinson, 3% (w/v) of betamethasone sodium phosphate solution were prepared by using each solution as obtained above. Moreover, at 4° C., 40° C., 50° C. and 60° C., the stability of the chemical drug after 2 weeks, after 1 month, after 4 months and after 6 months were also examined. The table 6 gives a result that at 4° C. and 60° C., the stability of the chemical drug after 2 weeks were examined. The table 7 gives a result that at 4° C., 40° C., 50° C. and 60° C., the stability of the chemical drug after 1 month were examined. The table 8 gives a result that at 4° C., 40° C., 50° C. and 60° C., the stability of the chemical drug after 4 months were examined. The table 9 gives a result that at 4° C., 40° C. and 50° C., the stability of the chemical drug after 6 months were examined. In the tables, W means a purified water (ion-exchange water), N2—W means a purified water which the bubbling is carried out with the nitrogen gas.

Moreover, the FIG. 1 gives a residual ratio of the chemical drug at 40° C. after 6 months. It is revealed that a residual ratio of the chemical drug is gradually increased from greater or equal to pH 5 from the FIG. 1.

TABLE 6

| initial con. theoritical value | pair theoritical value | % | Mean | SD |
|---|---|---|---|---|
| 4° C. 2 weeks | | | | |
| 3.01 | pH 2 | 74.85 74.26 77.40 | 75.50 | 1.36 |
| 3.02 | pH 3 | 86.95 85.74 82.99 | 85.23 | 1.66 |
| 3.01 | pH 4 | 89.30 89.20 89.77 | 89.42 | 0.25 |
| 3.01 | pH 5 | 95.39 97.02 90.60 | 94.34 | 2.72 |
| 3.01 | pH 6 | 99.84 100.97 95.90 | 98.90 | 2.17 |
| 3.01 | pH 7 | 101.38 98.04 101.26 | 100.23 | 1.55 |
| 3.01 | pH 8 | 103.84 108.89 102.01 | 104.91 | 2.91 |
| 3.02 | W | 99.96 101.82 101.37 | 101.05 | 0.79 |
| 3.02 | N2-W | 98.35 100.42 98.83 | 99.20 | 0.89 |
| 60° C. 2 weeks | | | | |
| 3.01 | pH 2 | 41.88 41.86 42.36 | 42.03 | 0.23 |
| 3.02 | pH 3 | 49.96 50.90 50.26 | 50.37 | 0.39 |
| 3.01 | pH 4 | 52.23 52.47 52.43 | 52.38 | 0.10 |
| 3.01 | pH 5 | 56.09 56.09 57.36 | 56.51 | 0.60 |
| 3.01 | pH 6 | 70.20 70.57 69.19 | 69.99 | 0.59 |
| 3.01 | pH 7 | 86.90 89.78 84.99 | 87.22 | 1.97 |
| 3.01 | pH 8 | 96.93 95.35 95.11 | 95.80 | 0.81 |
| 3.02 | W | 85.90 85.10 86.08 | 85.69 | 0.43 |
| 3.02 | N2-W | 90.31 94.65 90.31 | 91.76 | 2.05 |

TABLE 7

| initial con. theoritical value | pair theoritical value | % | Mean | SD |
|---|---|---|---|---|
| 4° C. 1 month | | | | |
| 3.01 | pH 2 | 81.26 83.19 80.39 | 81.61 | 1.17 |
| 3.02 | pH 3 | 71.09 81.96 94.34 | 82.46 | 9.50 |

TABLE 7-continued

| initial con. theoritical value | pair theoritical value | % | Mean | SD |
|---|---|---|---|---|
| 3.01 | pH 4 | 94.99 | 95.85 | 1.05 |
|  |  | 97.32 |  |  |
|  |  | 95.23 |  |  |
| 3.01 | pH 5 | 100.45 | 93.36 | 10.26 |
|  |  | 100.78 |  |  |
|  |  | 78.85 |  |  |
| 3.01 | pH 6 | 99.74 | 104.98 | 3.71 |
|  |  | 107.68 |  |  |
|  |  | 107.52 |  |  |
| 3.01 | pH 7 | 110.67 | 110.30 | 1.08 |
|  |  | 111.39 |  |  |
|  |  | 108.83 |  |  |
| 3.01 | pH 8 | 108.38 | 97.51 | 7.70 |
|  |  | 91.54 |  |  |
|  |  | 92.60 |  |  |
| 3.02 | W | 89.52 | 101.42 | 8.48 |
|  |  | 106.11 |  |  |
|  |  | 108.65 |  |  |
| 3.02 | N2- W | 108.45 | 107.68 | 0.55 |
|  |  | 107.31 |  |  |
|  |  | 107.27 |  |  |
| 40° C. 1 month |  |  |  |  |
| 3.01 | pH 2 | 63.48 | 62.65 | 0.68 |
|  |  | 62.67 |  |  |
|  |  | 61.81 |  |  |
| 3.02 | pH 3 | 72.69 | 82.48 | 6.93 |
|  |  | 87.84 |  |  |
|  |  | 86.92 |  |  |
| 3.01 | pH 4 | 91.16 | 81.36 | 6.94 |
|  |  | 76.94 |  |  |
|  |  | 75.97 |  |  |
| 3.01 | pH 5 | 78.88 | 78.88 | 0.64 |
|  |  | 79.66 |  |  |
|  |  | 78.09 |  |  |
| 3.01 | pH 6 | 84.81 | 86.51 | 5.53 |
|  |  | 80.75 |  |  |
|  |  | 93.97 |  |  |
| 3.01 | pH 7 | 89.10 | 89.32 | 0.22 |
|  |  | 89.24 |  |  |
|  |  | 89.62 |  |  |
| 3.01 | pH 8 | 90.86 | 90.10 | 0.67 |
|  |  | 90.21 |  |  |
|  |  | 89.22 |  |  |
| 3.02 | W | 87.34 | 96.79 | 6.69 |
|  |  | 101.17 |  |  |
|  |  | 101.87 |  |  |
| 3.02 | N2- W | 86.56 | 85.82 | 1.49 |
|  |  | 83.74 |  |  |
|  |  | 87.16 |  |  |
| 50° C. 1 month |  |  |  |  |
| 3.01 | pH 2 | 49.63 | 55.83 | 4.39 |
|  |  | 58.72 |  |  |
|  |  | 59.16 |  |  |
| 3.02 |  | 68.34 | 64.66 | 5.03 |
|  |  | 68.10 |  |  |
|  |  | 57.54 |  |  |
| 3.01 | pH 4 | 60.44 | 63.08 | 3.63 |
|  |  | 60.59 |  |  |
|  |  | 68.21 |  |  |
| 3.01 | pH 5 | 74.69 | 75.05 | 0.90 |
|  |  | 76.28 |  |  |
|  |  | 74.17 |  |  |
| 3.01 | pH 6 | 83.63 | 75.38 | 5.83 |
|  |  | 71.13 |  |  |
|  |  | 71.39 |  |  |
| 3.01 | pH 7 | 80.40 | 86.96 | 8.96 |
|  |  | 80.85 |  |  |
|  |  | 99.64 |  |  |
| 3.01 | pH 8 | 104.44 | 103.57 | 3.04 |
|  |  | 106.77 |  |  |
|  |  | 99.49 |  |  |
| 3.02 | W | 78.85 | 78.74 | 0.57 |
|  |  | 78.00 |  |  |
|  |  | 79.38 |  |  |
| 3.02 | N2- W | 84.40 | 89.72 | 3.95 |
|  |  | 90.89 |  |  |
|  |  | 93.85 |  |  |
| 60° C. 1 month |  |  |  |  |
| 3.01 | pH 2 | 14.76 | 14.90 | 0.79 |
|  |  | 15.92 |  |  |
|  |  | 14.01 |  |  |
| 3.02 | pH 3 | 16.81 | 17.55 | 0.72 |
|  |  | 17.31 |  |  |
|  |  | 18.53 |  |  |
| 3.01 | pH 4 | 19.07 | 19.17 | 0.11 |
|  |  | 19.12 |  |  |
|  |  | 19.32 |  |  |
| 3.01 | pH 5 | 16.59 | 17.09 | 0.46 |
|  |  | 17.70 |  |  |
|  |  | 16.97 |  |  |
| 3.01 | pH 6 | 28.15 | 25.28 | 2.03 |
|  |  | 23.67 |  |  |
|  |  | 24.02 |  |  |
| 3.01 | pH 7 | 36.78 | 36.13 | 0.46 |
|  |  | 35.74 |  |  |
|  |  | 35.88 |  |  |
| 3.01 | pH 8 | 43.39 | 45.01 | 1.56 |
|  |  | 47.12 |  |  |
|  |  | 44.53 |  |  |
| 3.02 | W | 33.46 | 33.60 | 0.15 |
|  |  | 33.54 |  |  |
|  |  | 33.81 |  |  |
| 3.02 | N2- W | 37.65 | 38.91 | 1.04 |
|  |  | 40.19 |  |  |
|  |  | 38.90 |  |  |

TABLE 8

| initial con. theoritical value | pair theoritical value | % | Mean | SD |
|---|---|---|---|---|
| 4° C. 4 month |  |  |  |  |
| 3.01 | pH 2 | 124.46 | 121.42 | 6.91 |
|  |  | 127.96 |  |  |
|  |  | 111.86 |  |  |
| 3.02 | pH 3 | 106.40 | 104.26 | 1.89 |
|  |  | 104.58 |  |  |
|  |  | 101.80 |  |  |
| 3.01 | pH 4 | 107.20 | 108.15 | 0.97 |
|  |  | 109.49 |  |  |
|  |  | 107.78 |  |  |
| 3.01 | pH 5 | 109.79 | 109.24 | 1.01 |
|  |  | 107.82 |  |  |
|  |  | 110.10 |  |  |
| 3.01 | pH 6 | 105.21 | 107.46 | 2.95 |
|  |  | 105.53 |  |  |
|  |  | 111.63 |  |  |
| 3.01 | pH 7 | 107.18 | 105.27 | 6.68 |
|  |  | 96.31 |  |  |
|  |  | 112.32 |  |  |
| 3.01 | pH 8 | 105.90 | 108.32 | 2.77 |
|  |  | 106.87 |  |  |
|  |  | 112.20 |  |  |
| 3.02 | W | 105.91 | 110.24 | 3.68 |
|  |  | 114.90 |  |  |
|  |  | 109.92 |  |  |
| 3.02 | N2- W | 99.99 | 100.06 | 0.85 |
|  |  | 101.13 |  |  |
|  |  | 99.04 |  |  |
| 40° C. 4 month |  |  |  |  |
| 3.01 | pH 2 | 56.68 | 57.15 | 0.35 |
|  |  | 57.21 |  |  |
|  |  | 57.55 |  |  |

TABLE 8-continued

| initial con. theoritical value | pair theoritical value | % | Mean | SD |
|---|---|---|---|---|
| 3.02 | pH 3 | 72.67 / 73.43 / 73.88 | 73.33 | 0.50 |
| 3.01 | pH 4 | 76.37 / 78.11 / 78.92 | 77.80 | 1.06 |
| 3.01 | pH 5 | 82.32 / 81.47 / 82.47 | 82.09 | 0.44 |
| 3.01 | pH 6 | 90.10 / 88.78 / 88.83 | 89.24 | 0.61 |
| 3.01 | pH 7 | 105.14 / 100.37 / 102.61 | 102.71 | 1.95 |
| 3.01 | pH 8 | 110.19 / 102.68 / 105.50 | 106.12 | 3.10 |
| 3.02 | W | 102.96 / 94.88 / 105.14 | 100.99 | 4.41 |
| 3.02 | N2-W | 105.83 / 103.94 / 91.13 | 100.30 | 6.53 |
| 50° C. 4 month | | | | |
| 3.01 | pH 2 | 22.74 / 21.34 / 23.25 | 22.44 | 0.81 |
| 3.02 | pH 3 | 32.72 / 32.89 / 32.91 | 32.84 | 0.08 |
| 3.01 | pH 4 | 33.24 / 32.85 / 29.30 | 31.80 | 1.77 |
| 3.01 | pH 5 | 32.42 / 33.20 / 33.02 | 32.88 | 0.33 |
| 3.01 | pH 6 | 48.53 / 32.32 / 43.59 | 41.48 | 6.78 |
| 3.01 | pH 7 | 69.24 / 63.11 / 67.12 | 66.49 | 2.54 |
| 3.01 | pH 8 | 79.44 / 81.81 / 90.11 | 83.79 | 4.57 |
| 3.02 | W | 71.01 / 69.80 / 71.82 | 70.87 | 0.83 |
| 3.02 | N2-W | 75.32 / 80.27 / 77.28 | 77.62 | 2.03 |
| 60° C. 4 month | | | | |
| 3.01 | pH 2 | 2.78 / 2.81 / 2.77 | 2.79 | 0.01 |
| 3.02 | | 3.49 / 3.50 / 3.40 | 3.46 | 0.04 |
| 3.01 | pH 4 | 3.35 / 3.38 / 3.40 | 3.38 | 0.02 |
| 3.01 | pH 5 | 3.42 / 3.31 / 3.30 | 3.34 | 0.06 |
| 3.01 | pH 6 | 5.71 / 5.88 / 5.96 | 5.85 | 0.10 |
| 3.01 | pH 7 | 24.45 / 25.55 / 27.12 | 25.71 | 1.10 |
| 3.01 | pH 8 | 62.41 / 61.79 / 61.76 | 61.99 | 0.30 |
| 3.02 | W | 17.45 / 17.11 / 18.44 | 17.67 | 0.57 |
| 3.02 | N2-W | 31.07 / 47.38 / 47.45 | 41.97 | 7.71 |

TABLE 9

| initial con. theoritical value | pair theoritical value | % | Mean | SD |
|---|---|---|---|---|
| 4° C. 6 month | | | | |
| 3.01 | pH 2 | 54.96 / 56.94 / 57.54 | 56.48 | 1.11 |
| 3.02 | pH 3 | 76.56 / 73.84 / 74.37 | 74.92 | 1.18 |
| 3.01 | pH 4 | 81.91 / 81.09 / 80.95 | 81.32 | 0.42 |
| 3.01 | pH 5 | 90.92 / 91.49 / 90.15 | 90.85 | 0.55 |
| 3.01 | pH 6 | 98.55 / 97.44 / 96.81 | 97.60 | 0.72 |
| 3.01 | pH 7 | 101.67 / 101.53 / 100.93 | 101.38 | 0.32 |
| 3.01 | pH 8 | 101.67 / 102.74 / 105.45 | 103.29 | 1.59 |
| 3.02 | W | 97.06 / 98.18 / 98.80 | 98.01 | 0.72 |
| 3.02 | N2-W | 100.01 / 96.68 / 98.12 | 98.27 | 1.36 |
| 40° C. 6 month | | | | |
| 3.01 | pH 2 | 32.91 / 32.94 / 33.73 | 33.20 | 0.38 |
| 3.02 | pH 3 | 50.35 / 49.33 / 50.31 | 50.00 | 0.47 |
| 3.01 | pH 4 | 54.23 / 53.19 / 52.24 | 53.22 | 0.81 |
| 3.01 | pH 5 | 58.24 / 56.82 / 56.57 | 57.21 | 0.74 |
| 3.01 | pH 6 | 68.30 / 67.56 / 67.25 | 67.70 | 0.44 |
| 3.01 | pH 7 | 84.61 / 86.09 / 83.98 | 84.89 | 0.88 |
| 3.01 | pH 8 | 95.43 / 92.49 / 92.27 | 93.40 | 1.44 |
| 3.02 | W | 85.70 / 86.06 / 83.26 | 85.01 | 1.24 |
| 3.02 | N2-W | 85.74 / 86.00 / 89.47 | 87.07 | 1.70 |

TABLE 9-continued

| initial con. theoritical value | pair theoritical value | | |
|---|---|---|---|
| | | % Mean | SD |
| 50° C. 6 month | | | |
| 3.01 | pH 2 | 8.17 8.31 | 0.11 |
| | | 8.34 | |
| | | 8.44 | |
| 3.02 | pH 3 | 14.21 14.20 | 0.01 |
| | | 14.19 | |
| | | 14.21 | |
| 3.01 | pH 4 | 14.68 14.73 | 0.08 |
| | | 14.67 | |
| | | 14.85 | |
| 3.01 | pH 5 | 15.07 14.84 | 0.19 |
| | | 14.62 | |
| | | 14.82 | |
| 3.01 | pH 6 | 24.16 24.39 | 0.21 |
| | | 24.33 | |
| | | 24.67 | |
| 3.01 | pH 7 | 54.84 54.28 | 0.53 |
| | | 54.42 | |
| | | 53.57 | |
| 3.01 | pH 8 | 77.56 78.19 | 0.84 |
| | | 77.64 | |
| | | 79.38 | |
| 3.02 | W | 49.56 49.86 | 0.47 |
| | | 49.50 | |
| | | 50.53 | |
| 3.02 | N2-W | 62.36 63.27 | 5.20 |
| | | 57.41 | |
| | | 70.04 | |

As a result of these, it was revealed that the stability of the chemical drug is also increased according to the increase of pH value.

Example 6

Next, the distribution of the $^3$H labeled betamethasone sodium phosphate was examined by preparing a semimicroautoradiograph of a normal rabbit knee arthrosis which the treatment of the power distribution is carried out, after transdermally administering the $^3$H labeled betamethasone sodium phosphate.

The radioactive concentration in the blood plasma of a rabbit was examined after it is transdermally administered in association with the power distribution. In the individual organism administered for 120 minutes, the radioactive concentration in the blood plasma gradually rose from 10 minutes after administered, and it showed a maximum numeric value after 120 minutes, and it still tended to rise. In the individual organism administered for 30 minutes, the radioactive concentration in the blood plasma gradually rose from 10 minutes after administered, and it showed that it still tended to rise in the 30 minutes after administered.

The semimicroautoradiographs of a rabbit knee arthrosis in the case that the administration time is 120 minutes and 30 minutes were prepared. When it focus attention on, in particular, a synovial joint among a skeletal system tissue, a mark of a blackened image according to $^3$H, although it is very slight amount, was recognized at a fibrous encapsulation and a synovium membrane.

Concerning a cingulum of the perimysial tissue (perimysium), a blackened image having a high density according to $^3$H which was existing up to the reticular dermis located in the inner side of the epidermal tissue, was observed, and further the blackened image of the outer circumference of the perimysium was also observed.

Regarding the semimicroautoradiograph of a knee arthrosis in the case of non-administration and non-treatment, in the individual organism administered for 120 minutes, although it was confirmed of the very poor blackened image of epithelial tissue, any of them was at background level, it was impossible to measure the intensity of the radioactivity.

From the above result, it was shown that it was absorbed in the deep portion according to the transdermally administration of the $^3$H labeled betamethasone sodium phosphate in association with the treatment of applying current. It was revealed of not only the migration to the inner skin capillary blood vessel, but the migration to the inner side of the perimysium and the synovium through the perimysium from the supporting layer.

As the examination item, a purity determination of the labeled compound, a determination of the radioactive concentration in the blood plasma, the semimicroautoradiographs of a rabbit knee arthrosis, the semimicroautoradiographs of a rabbit knee arthrosis (at non-administered portion), were carried out.

<A Purity Determination of the Labeled Compound>

The table 10 shows the content of the purity determination of the labeled compound.

TABLE 10

| examination item | test substance method | timepoint of observation |
|---|---|---|
| radiochemical purity assey of labeled compound | [$^3$H] TLC method Betamethasone-21-phosphate disodium salt | when taking compound when stating test |

<A Determination of the Radioactive Concentration in the Blood Plasma>

The table 11 shows the content of the determination of the radioactive concentration in the blood plasma.

TABLE 11

| animal(weight) | sex | n number | time point of observation |
|---|---|---|---|
| rabbit (2.0~2.5 kg) | male | 1 | 10 min, 20 min, 30 min |
| rabbit (2.0~2.5 kg) | male | 1 | 10 min, 20 min, 30 min, 60 min, 90 min, 120 min |

Moreover, the condition of the transdermally administration in association with the treatment of applying current is as follows. The applied dose: 18.5 MBq (500 μCi)/1 mL/head.

<The Semimicroautoradiographs of a Rabbit Knee Arthrosis>

The table 12 shows the content of the semimicroautoradiographs of a rabbit knee arthrosis.

TABLE 12

| animal(weight) | sex | n number | time point of observation |
|---|---|---|---|
| rabbit (2.0~2.5 kg) | male | 1 | administration for 30 min., after treatment |
| rabbit (2.0~2.5 kg) | male | 1 | administration for 120 min., after treatment |

Moreover, the condition of the transdermally administration in association with the treatment of applying current is as follows. The applied dose: 18.5 MBq (500 μCi)/1 mL/head.

<The Semimicroautoradiographs of a Rabbit Knee Arthrosis (at Non-Administered Portion)>

The table 13 shows the content of the semimicroautoradiographs of a rabbit knee arthrosis (at non-administered portion).

TABLE 13

| animal(weight) | sex | n number | time point of observation |
|---|---|---|---|
| rabbit (2.0~2.5 kg) | male | 1 | administration for 30 min., after treatment |
| rabbit (2.0~2.5 kg) | male | 1 | administration for 120 min., after treatment |

<The Labeled Compound>

The labeled compound is as followed.

The name of the labeled compound: [$^3$H] Betamethasone-21-phosphate disodium salt
  Provider: GE Healthcare Japan Corporation
  Radiochemical purity: 99.4%
  Radioactive concentration: 185 MBq (5 mCi)/mL
  Specific radioactivity: 407 GBq (11 Ci)/mmol
  Form: liquid
  Storing method: light shielding, air sealing, freezer storage (−20° C.)

As to the other reagent, the high grade product, or product of similar quality, and the standard product for HPLC (high-performance liquid chromatography) were used.

<The Purity Determination of [$^3$H] Betamethasone-21-Phosphate Disodium Salt>

In order to determine the radiochemical purity of [$^3$H] Betamethasone-21-phosphate disodium salt, the assay was carried out by using the TLC method when taking the compound (lot number TRQ40214). The analysis conditions are as follows.

<The Analysis Conditions of TLC>
  Assay date: Nov. 18, 2008 (when taking the compound)
  TLC plate: Silica gel 60 $F_{254}$ (Merck)
  Mobile Phase: n-BuOH/AcOH/DW (8:1:1)

<The Preparation of the Gel Drug Formulation>

About 18.5 MBq (500 mCi/1 g) of a gel of [$^3$H]-Betamethasone-21-phosphate disodium salt was prepared. A mixed solution of the tritium labeled [$^3$H]-Betamethasone-21-phosphate disodium salt and the non labeled [$^3$H]-Betamethasone-21-phosphate disodium salt was prepared, and mixed with the molten PVA solution. This was funneled into a patch comprising an electrode and an adhesion layer, and cooled down at −80° C. to obtain a desired drug product.

<The Test Animal>

Two NZ family male rabbits to be devoted to the test was bought from KITAYAMA LABES Co., Ltd., (Charles River Japan, Inc.). The rabbits were given a houseroom with 1 rabbit per 1 gauge, and preliminary bred for 3 days, and used for the test after it was confirmed that they are in good physical health (the weight of the rabbit: 2.49 kg and 2.43 kg). The observation of the animal during the preliminary breeding and the test, as to a hair coat, a skin and a excretory substance was carried out every day.

When the animal were received, the animals were labeled by assigning a number to the ear of the animal. For the test, the rabbits were randomly-assigned into groups. The animals were given a houseroom made of the metal gauge (400 W×500 D×400H mm, Natsume Seisakusho Co., Ltd.) and bred. The exchange of the gauge, the floorcloth, the feeder and the bottle for feeding water were carried out at 3 times per week. The breeding during the preliminary breeding and the test was carried out in a feeding room set at 19.0° C. to 23.6° C. of the temperature, 40.0 to 60.0% RH of the degree of humidity, 12 hours/12 hours light-dark cycle (light: 6:00 to 18:00, dark: 18:00 to 6:00 on following morning), the animal feeding stuff (feeding for the rabbit (LRC −4, Oriental Yeast Co., Ltd.) and the water was freely uptook.

<The Administration Method and the Applied Dose>

The administration method and the applied dose were as follows.

The administration route: the transdermally administration in association with the treatment of applying current The applied dose: 18.5 MBq (500 μCi)/1 mL/head <The Treatment of Applying Current for the Administration Portion>

Figure 4:
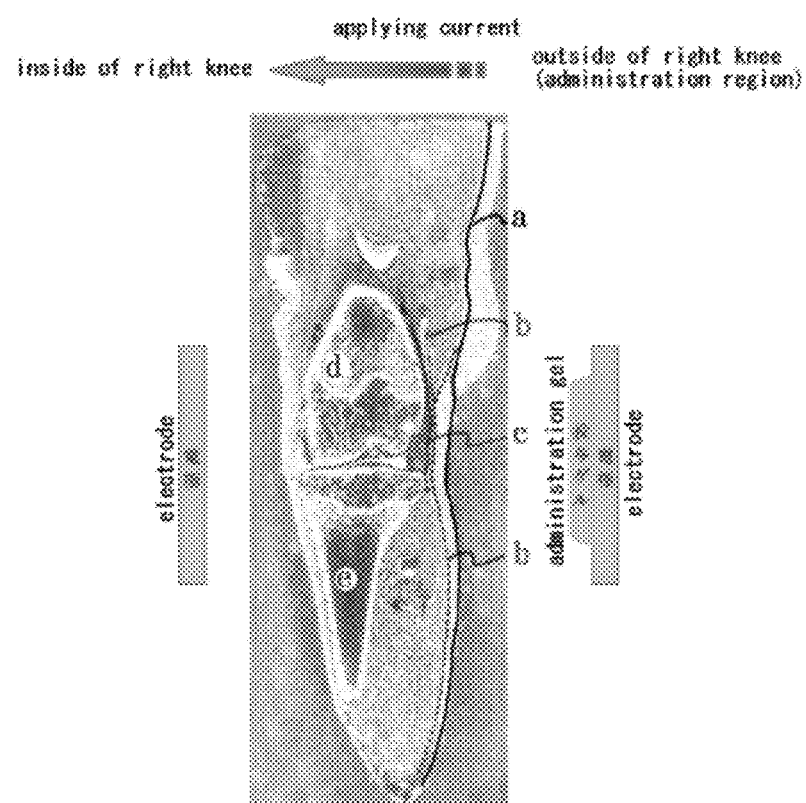
FIG. 4 gives pattern diagrams of a normal rabbit right knee arthrosis wherein the 3H labeled betamethasone sodium phosphate is administered transdermally by applying current.

The gel drug product of the $^3$H labeled betamethasone sodium phosphate (negative electrode) and the reference gel drug product containing no chemical drug (positive electrode) were applied to the preliminary dehaired rabbit knee arthrosis, and this was connected to the energization system (VI 1002, PRECISE GAUGES co., ltd.). It was applied 0.968 mA of current (0.2 mA/cm² of the current density) for 30 minutes or 120 minutes. The FIG. 4 gives a pattern diagrams of the treatment of applying current. The FIG. 4 gives a pattern diagrams of a normal rabbit knee arthrosis wherein the $^3$H labeled betamethasone sodium phosphate is transdermally administered by applying current. The electrode A was used for an individual which was administered for 120 minutes, and the electrode B was used for an individual which was administered for 30 minutes (table 14). The table 14 shows a radioactivity in the gel containing drug solution or chemical drug and amount of the drug.

TABLE 14

| | | HOT + COLD the amount of radioactivity of drug solution | | | | | | |
|---|---|---|---|---|---|---|---|---|
| | | ×1000 dilute solution | | | | | HOT + COLD drug solution | |
| | sampling amount | countable number of values | RI$^{density}$ | | | | RI density | |
| dilute solution | μL | dpm | dpm/mL | AV dpm/mL | ±SD | % RSD | mCi/mL | dpm/mL |
| ① | 10 | 49567 | 4956700 | 4891550 | 45608 | 0.93 | 2.203 | 4891550000 |
| | 10 | 48626 | 4862600 | | | | | |
| ② | 10 | 48576 | 4857600 | | | | | |
| | 10 | 48893 | 4889300 | | | | | |

TABLE 14-continued

HOT + COLD the amount of radioactivity of drug solution the amount of radioactivity of gel containing drug

| electrode | additive amount of drug | | | adjusting | | | collection quantity of gel into electrode | | |
|---|---|---|---|---|---|---|---|---|---|
| | liquid amount mL | amount of radio- activity μCi | drug amount mg | amount of gel g | gel RI density μCi/g | gel drug con. mg/g | weight g | amount of radio- activity μCi | drug amount mg |
| A | 0.264 | 581.6 | 34.9 | 1.3533 | 429.8 | 25.8 | 1.2695 | 545.6 | 32.7 |
| B | 0.262 | 577.2 | 34.6 | 1.3510 | 427.2 | 25.6 | 1.2603 | 538.4 | 32.3 |

The radioactivity density assay in the blood plasma was carried out as follows. At the predetermined time point after administration, using a syringe executed with the heparin treatment, a withdrawn blood was be separated by centrifugalization (4° C., 3000 rpm, 15 minutes) to prepare a blood plasma, and to obtain a sample for the radioactivity measurement.

A sample for assay was treated by adding the solubilizing agent, and the measurement of the sample was carried out by using the liquid scintillation counter (LSC-1000, ALOKA). The limit of determinate quantity was two folds of the background, and the lesser value of the limit was determined as ND. The radioactivity density assay in the blood plasma was calculated from the measured value.

Next, a semimicroautoradiograph of a rabbit knee arthrosis was prepared as follows.

After 30 minutes and 120 minutes of the administration, each of the animals was put out of the misery by excessively administering the anesthetic drug (Nembutal), and a portion of knee arthrosis was removed from the animals and freezed up by using liquid nitrogen. After that, an embedded freezing block was directed to the cutter of the microtome stage for mounting (CRYOMACROCUT, Leica), and a femoral region thereof was directed to the front, and a neck region was directed to the backside, and was fixed with being in close contact with the backside of the leg to the stage for mounting. When the stage for mounting of microtome was slid, the cutter was contacted perpendicular with the narrow side of the rectangular, the upper surface of this was chipped off as a sliced segment, the sliced segment was in close contact to the adhesive tape, and removed. This operation was repeated a couple dozens times, it was cleaved from the front portion of the knee to the backside portion, a segment of the administration and current-carrying part was (1) to (7) (from the front to the backside) in order of precedence. An interested segment was contact exposed with the imaging plate (Fujifilm Corporation), and after the exposure for 168 hours, a two-dimensional picture thereof was created by the bio imaging analyzer (BAS1800, Fujifilm Corporation).

The radioactivity density is used as indication pointer, the calibrated concentration of the chemical drug converted with unaltered substance was calculated by the following formula.

The calibrated concentration of the chemical drug (μg eq./mL)=The radioactivity density in the sample (dpm/mL)/{the amount of the administration radioactivity (dpm)/the amount of the administration chemical drug (μg)}

Each result of the assay was as follows.
<Concerning the Assay of the Radioactivity Density in the Blood Plasma>

The radioactivity density in the blood plasma of the rabbit after the $^3$H labeled betamethasone sodium phosphate was transdermally administered by applying current was shown in the table 15. The table 15 shows the radioactivity density in the blood plasma of the rabbit after the $^3$H labeled betamethasone sodium phosphate is transdermally administered or treated by applying current.

TABLE 15

| | 120 min. administration individual | | 30 min. administration individual | |
|---|---|---|---|---|
| Time point of observation (minutes) | average of radioactivity density (dpm/mL) | average of drug conversion (μg eq./mL) | average of radioactivity density (dpm/mL) | average of drug conversion (μg eq./mL) |
| 10 | 1473.0 | 0.04 | 271 | 0.01 |
| 20 | 3467.0 | 0.09 | 937 | 0.03 |
| 30 | 8575.0 | 0.23 | 3155 | 0.09 |
| 60 | 24502.2 | 0.66 | | |
| 90 | 33662.0 | 0.91 | | |
| 120 | 43142.0 | 1.17 | | |

In the individual organism administered for 120 minutes, the radioactive concentration in the blood plasma gradually rose from 10 minutes after administered, and it showed a maximum numeric value after 120 minutes, and it still tended to rise. The average converted value of the chemical drug was 1.17 μg eq/mL. In the individual organism administered for 30 minutes, the radioactive concentration in the blood plasma also rose gradually from 10 minutes after administered, and it showed that it still tended to rise in the 30 minutes after administered. The average converted value of the chemical drug was 0.09 μg eq/mL.

<As to the Semimicroautoradiograph of a Rabbit Knee Arthrosis>

The pattern diagrams of a normal rabbit right knee arthrosis wherein the $^3$H labeled betamethasone sodium phosphate is administered transdermally by applying current toward inner side of the knee arthrosis from out side was shown in FIG. 4. The degree of the blackened image of an epithelium, a perimysia, a periosteum, a bone and a bone marrow etc., was examined.

Figure 5:
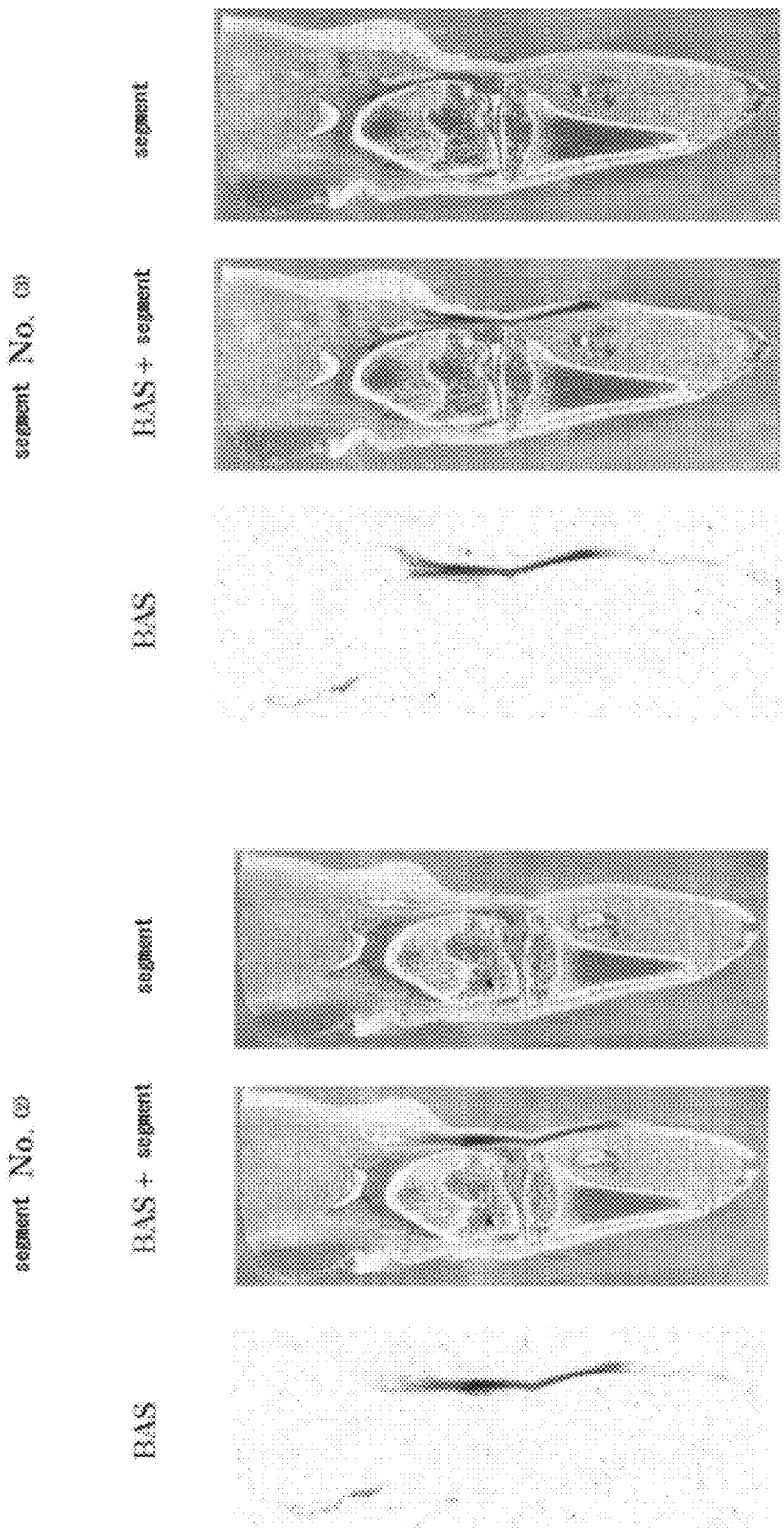
FIG. 5 gives a semimicroautoradiograph of a normal rabbit right knee arthrosis wherein the 3H labeled betamethasone sodium phosphate is administered transdermally at 30 minutes by applying current.
Figure 6:
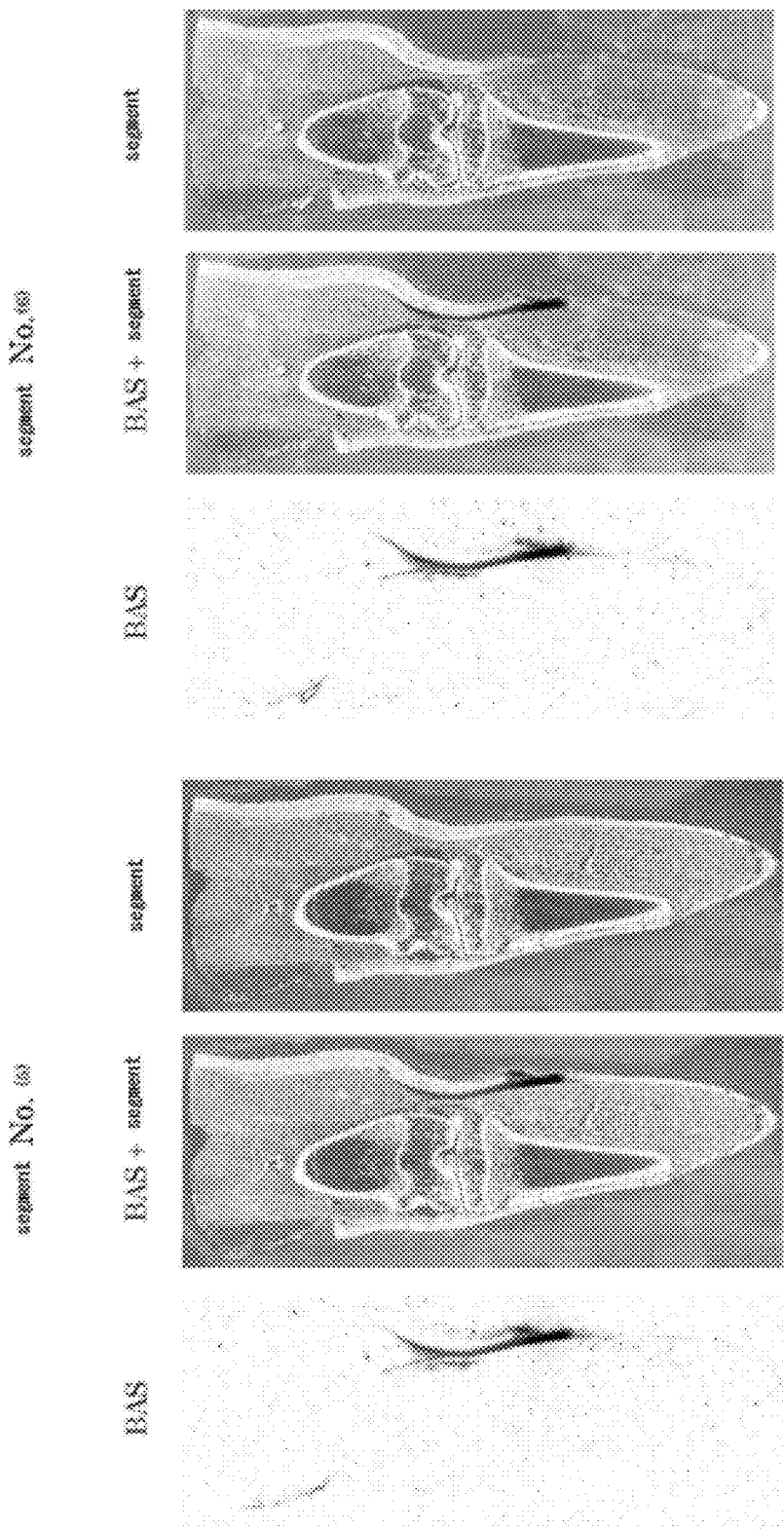
FIG. 6 gives a semimicroautoradiograph of a normal rabbit right knee arthrosis wherein the 3H labeled betamethasone sodium phosphate is administered transdermally at 30 minutes by applying current.
Figure 7:
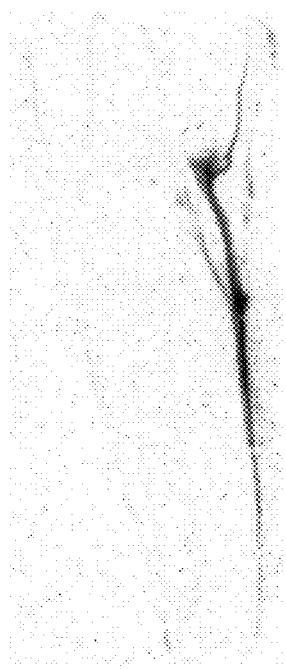
FIG. 7 gives a semimicroautoradiograph of a normal rabbit right knee arthrosis wherein the 3H labeled betamethasone sodium phosphate is administered transdermally at 120 minutes by applying current.
Figure 7:
Figure 7:

The semimicroautoradiographs of a rabbit right knee arthrosis administered for 30 minutes were shown in the FIGS. 5 and 6, and the semimicroautoradiograph of a rabbit right knee arthrosis administered for 120 minutes were shown in the FIG. 7. The semimicroautoradiograph according to the BAS1800 at left side, the segment image at right side, and the synthetic image which was obtained by lapping over the BAS image to the segment image, were shown.

In the individual organism administered for 30 minutes, the cross-section surface of the segment number (2), (3), (5) and (6) in order of precedence which was cleaved from the front portion of the knee to the backside portion, were shown, and in the individual organism administered for 120 minutes the segment number (5) was shown. In each segment, the radioactivity density [(PSL−BG)/area] of the 4 regions which was determined the quantity according to the degree of the blackened image, were shown in the table 16 (administration for 120 minutes) and in the table 17 (administration for 30 minutes).

TABLE 16 rabbit ① for 120 min.

| segment No. | maximum blackened region | outside of perimysia | inside of perimysia | articular capsule surrounding tissue |
|---|---|---|---|---|
| ⑤ | 807 | 39.93 | 18.03 | 0.41 |

TABLE 17 rabbit ② for 30 min.

| segment No. | maximum blackened region | outside of perimysia | inside of perimysia | articular capsule surrounding tissue |
|---|---|---|---|---|
| ② | 42.49 | 45.44 | 0.62 | 0.09 |
| ③ | 97.16 | 47.25 | 24.62 | 0.03 |
| ⑤ | 1091.13 | 49.69 | 13.87 | 0.42 |
| ⑥ | 843.74 | 57.07 | 12.3 | 0.3 |

When it focus attention on, in particular, a synovial joint among a skeletal system tissue, a mark of a blackened image according to $^3$H, although it is very slight amount, was recognized at a fibrous encapsulation and a synovium membrane.

Concerning a cingulum of the perimysial tissue (perimysium), a blackened image having a high density according to $^3$H which was existing up to the reticular dermis located in the inner side of the epidermal tissue, was observed, and further the blackened image of the outer circumference of the perimysium. This image arrived to a tendon, the blackened image was immersed to the inner circumference through the peripheral muscle and finally reached to the periostea.

The blackened concentration in this case was very poor. As shown in tables 16 and 17, regarding the example in the case of the administration for 120 minutes (cross section (5)), the intensities of radioactivity were 807.0 [PSL−BG/area] at the maximum blackened portion, 39.93 [PSL−BG/area] at the outside of perimysia, 18.03 [PSL−BG/area] at the inner side of perimysia, 0.41 [PSL−BG/area] at the articular capsule surrounding tissue, respectively. On the other hand, regarding the example in the case of the administration for 30 minutes (cross section (5)), the intensities of radioactivity were 1091.13 [PSL−BG/area] at the maximum blackened portion, 49.69 [PSL−BG/area] at the outside of perimysia, 13.87 [PSL−BG/area] at the inner side of perimysia, 0.42 [PSL−BG/area] at the articular capsule surrounding tissue, respectively.

<As to the Semimicroautoradiograph of a Rabbit Knee Arthrosis (Non-Administration Portion)>

Figure 8:
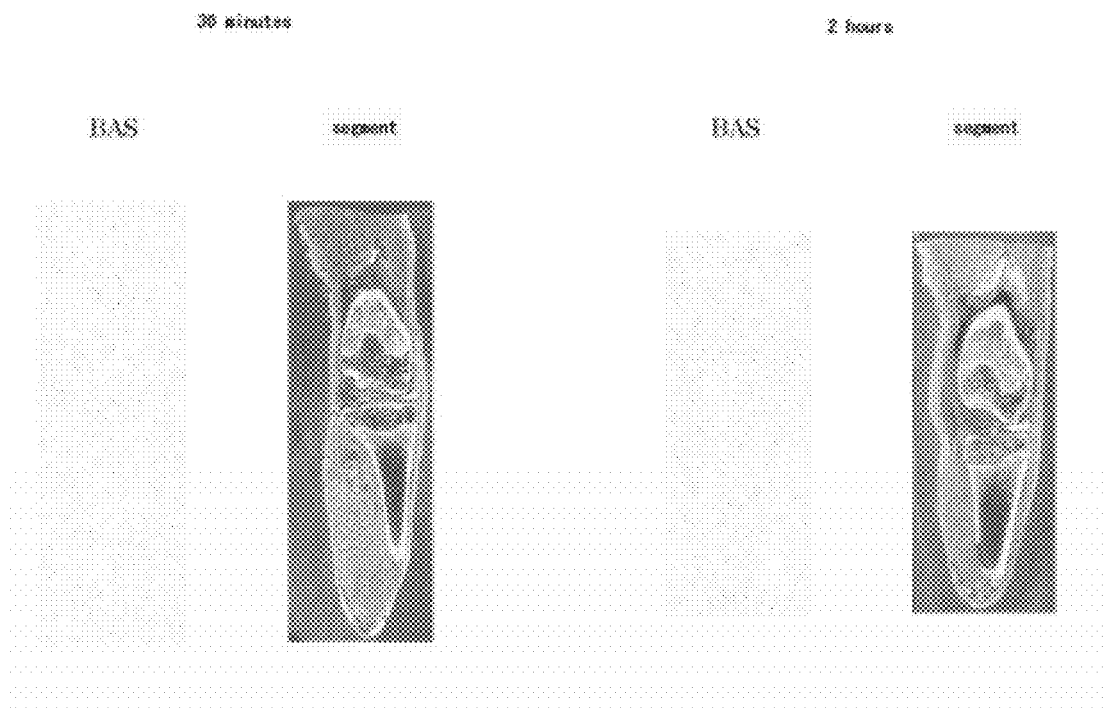
FIG. 8 gives a semimicroautoradiograph of a left knee arthrosis of the normal rabbit, that is, at the side of no administration, wherein the 3H labeled betamethasone sodium phosphate in the right leg is administered transdermally by applying current.

A semimicroautoradiograph of a knee arthrosis of non-administration and non-treatment is shown in the FIG. 8. In the individual organism administered for 120 minutes, as a result that the exposure was carried out for a long period, that is, for 168 hours, although it was confirmed of the very poor blackened image of epithelial tissue, but it was impossible to measure the intensity of the radioactivity because any of them was at background level.

In both examples, although the amounts of the administered radioactivity are almost the same amount between the 538.3908 μCi for the individual organism for 30 minutes and the 545.6088 μCi for the individual organism for 120 minutes, it was observed that in the individual organism for 30 minutes, there are a region showing a high density in the epithelium, and a region tissue in the epithelial wherein the concentration of the chemical drug is highly distributed with 1.35 folds, compared with in the individual organism for 120 minutes. Therefore, it is thought that in the individual organism for 30 minutes, the dispersion for total body is likely to be rapid according to the absorption from the epithelium.

From the result of the test, it was shown that it was absorbed in the deep portion according to the transdermally administration of the $^3$H labeled betamethasone sodium phosphate in association with the treatment of applying current. It was revealed of not only the migration to the inner skin capillary blood vessel, but the migration to the inner side of the perimysium and the synovium through the perimysium from the supporting layer.

Example 7

Figure 9:
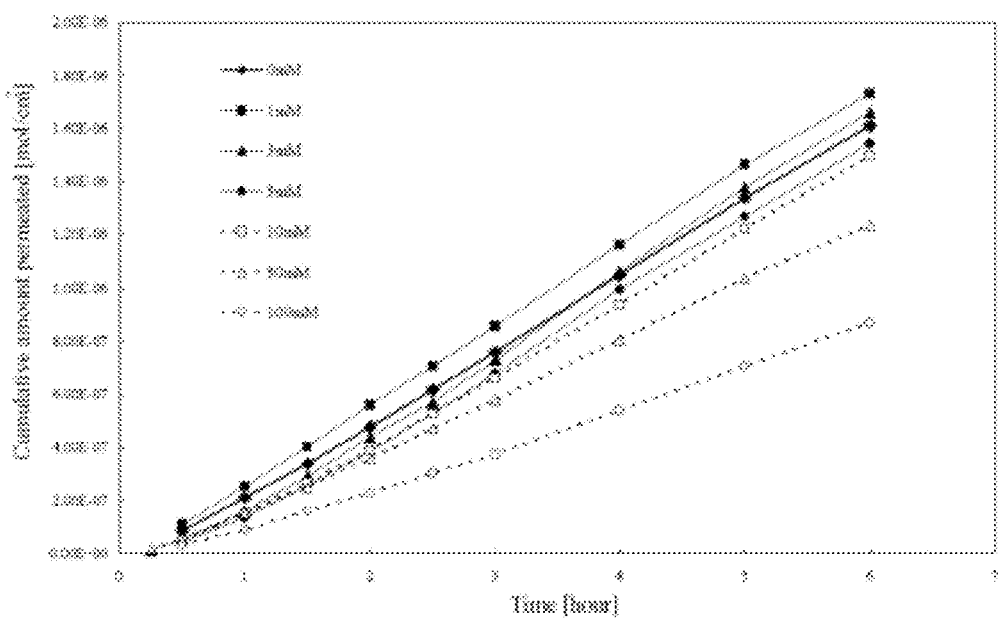
FIG. 9 gives a relationship between a cumulative amount permeated profile and a time in 0 mM to 100 mM of the concentration of phosphate.
Figure 10:
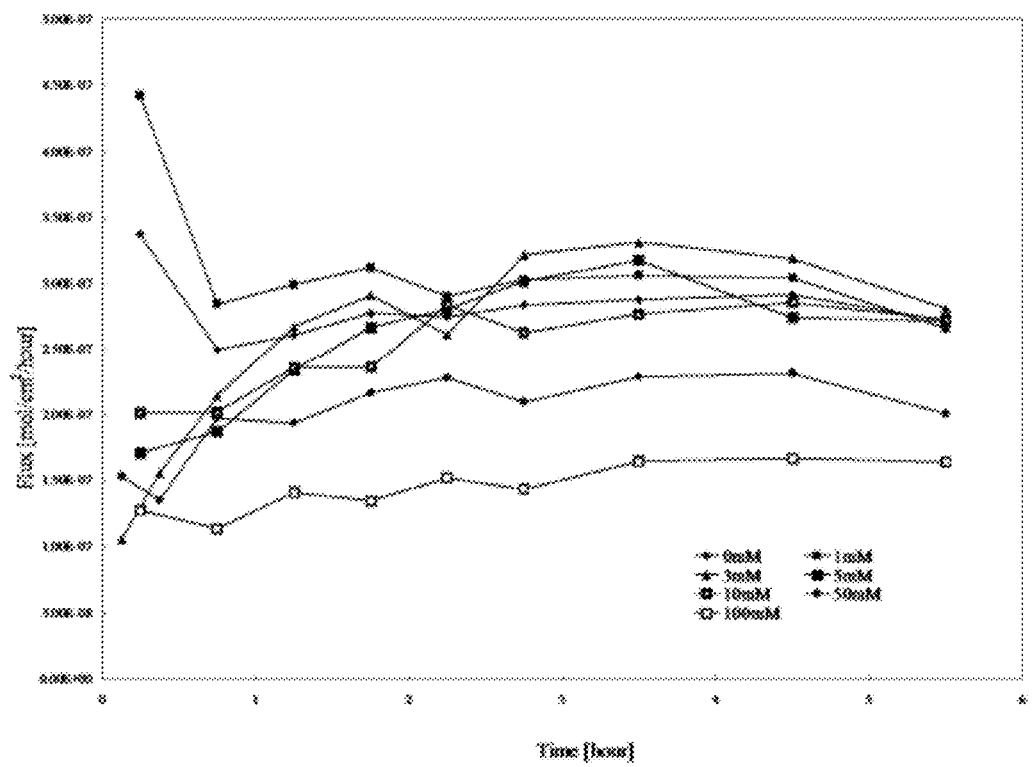
FIG. 10 gives a relationship between a time course flux and a time of a cumulative amount permeated profile in 0 mM to 100 mM of the concentration of phosphate.

Next, a skin permeability of a hair less mouse was examined in the case that the solvent used at the time of manufacturing the PVA gel is made for phosphate buffer solution (adjusted to pH 8), and 0 mM to 100 mM of the concentration of salt of phosphoric acid is prepared. The table 18 shows in the case of 0 mM of the concentration of salt of phosphoric acid. The table 19 shows in the case of 1 mM of the concentration of salt of phosphoric acid. The table 20 shows in the case of 3 mM of the concentration of salt of phosphoric acid. The table 21 shows in the case of 5 mM of the concentration of salt of phosphoric acid. The table 22 shows in the case of 10 mM of the concentration of salt of phosphoric acid. The table 23 shows in the case of 10 mM of the concentration of salt of phosphoric acid (at the second round). The table 24 shows in the case of 50 mM of the concentration of salt of phosphoric acid. The table 25 shows in the case of 100 mM of the concentration of salt of phosphoric acid. Furthermore, the FIG. 9 gives a relationship between an amount of the chemical drug accumulated in the skin and a time in 0 mM to 100 mM of the concentration of phosphate. The FIG. 10 gives a relationship between a time course flux and a time of a cumulative amount permeated profile in 0 mM to 100 mM of the concentration of phosphate. Moreover, in the tables 18 to 25, a unit of the cumulative permeated amount is a [mol/cm$^2$] (for example, No. 1 [mol/cm$^2$] etc.), a unit of the flux is a [mol/cm$^2$/hour].

TABLE 18

0 mM

| Time[hour] | No. 1 | No. 2 | No. 3 | Mean | S.D. |
|---|---|---|---|---|---|
| 0.5 | 6.78E−08 | 7.77E−08 | 1.08E−07 | 8.44E−08 | 2.08E−08 |
| 1 | 1.84E−07 | 2.07E−07 | 2.38E−07 | 2.10E−07 | 2.70E−08 |
| 1.5 | 3.11E−07 | 3.39E−07 | 3.72E−07 | 3.40E−07 | 3.06E−08 |
| 2 | 4.50E−07 | 4.77E−07 | 5.11E−07 | 4.79E−07 | 3.07E−08 |
| 2.5 | 5.85E−07 | 6.21E−07 | 6.45E−07 | 6.17E−07 | 2.99E−08 |
| 3 | 7.19E−07 | 7.58E−07 | 8.00E−07 | 7.59E−07 | 4.06E−08 |
| 4 | 9.99E−07 | 1.05E−06 | 1.09E−06 | 1.05E−06 | 4.61E−08 |
| 5 | 1.27E−06 | 1.34E−06 | 1.41E−06 | 1.34E−06 | 7.15E−08 |
| 6 | 1.52E−06 | 1.63E−06 | 1.68E−06 | 1.61E−06 | 8.00E−08 |
| Flux | | | | | |
| 0.25 | 2.71E−07 | 3.11E−07 | 4.31E−07 | 3.38E−07 | 8.34E−08 |
| 0.75 | 2.33E−07 | 2.58E−07 | 2.61E−07 | 2.51E−07 | 1.52E−08 |
| 1.25 | 2.52E−07 | 2.65E−07 | 2.67E−07 | 2.61E−07 | 7.91E−09 |
| 1.75 | 2.79E−07 | 2.76E−07 | 2.79E−07 | 2.78E−07 | 1.96E−09 |
| 2.25 | 2.71E−07 | 2.87E−07 | 2.67E−07 | 2.75E−07 | 1.08E−08 |

TABLE 18-continued

| 0 mM | | | | | |
|---|---|---|---|---|---|
| Time[hour] | No. 1 | No. 2 | No. 3 | Mean | S.D. |
| 2.75 | 2.67E−07 | 2.75E−07 | 3.11E−07 | 2.84E−07 | 2.33E−08 |
| 3.5 | 2.80E−07 | 2.94E−07 | 2.90E−07 | 2.88E−07 | 7.37E−09 |
| 4.5 | 2.67E−07 | 2.90E−07 | 3.18E−07 | 2.92E−07 | 2.56E−08 |
| 5.5 | 2.57E−07 | 2.90E−07 | 2.70E−07 | 2.72E−07 | 1.67E−08 |

TABLE 19

| 1 mM | | | | | |
|---|---|---|---|---|---|
| Time[hour] | no. 4 | no. 5 | no. 6 | Mean | S.D. |
| 0.5 | 8.06E−08 | 1.60E−07 | 9.12E−08 | 1.11E−07 | 4.32E−08 |
| 1 | 1.98E−07 | 3.39E−07 | 2.23E−07 | 2.53E−07 | 7.54E−08 |
| 1.5 | 3.31E−07 | 5.19E−07 | 3.59E−07 | 4.03E−07 | 1.01E−07 |
| 2 | 4.61E−07 | 7.01E−07 | 5.15E−07 | 5.59E−07 | 1.26E−07 |
| 2.5 | 5.84E−07 | 8.67E−07 | 6.61E−07 | 7.04E−07 | 1.46E−07 |
| 3 | 7.19E−07 | 1.03E−06 | 8.19E−07 | 8.56E−07 | 1.58E−07 |
| 4 | 1.00E−06 | 1.35E−06 | 1.14E−06 | 1.16E−06 | 1.73E−07 |
| 5 | 1.30E−06 | 1.67E−06 | 1.44E−06 | 1.47E−06 | 1.86E−07 |
| 6 | 1.55E−06 | 1.93E−06 | 1.72E−06 | 1.73E−06 | 1.92E−07 |
| Flux | | | | | |
| 0.25 | 3.22E−07 | 6.40E−07 | 3.65E−07 | 4.43E−07 | 1.73E−07 |
| 0.75 | 2.35E−07 | 3.58E−07 | 2.63E−07 | 2.85E−07 | 6.47E−08 |
| 1.25 | 2.67E−07 | 3.59E−07 | 2.72E−07 | 2.99E−07 | 5.20E−08 |
| 1.75 | 2.60E−07 | 3.64E−07 | 3.13E−07 | 3.12E−07 | 5.17E−08 |
| 2.25 | 2.46E−07 | 3.33E−07 | 2.93E−07 | 2.90E−07 | 4.34E−08 |
| 2.75 | 2.69E−07 | 3.25E−07 | 3.15E−07 | 3.03E−07 | 2.96E−08 |
| 3.5 | 2.84E−07 | 3.17E−07 | 3.17E−07 | 3.06E−07 | 1.93E−08 |
| 4.5 | 2.93E−07 | 3.19E−07 | 3.03E−07 | 3.05E−07 | 1.33E−08 |
| 5.5 | 2.54E−07 | 2.67E−07 | 2.77E−07 | 2.66E−07 | 1.15E−08 |

TABLE 20

| 3 mM | | | | | |
|---|---|---|---|---|---|
| Time[hour] | No. 1 | No. 2 | No. 3 | Mean | S.D. |
| Q[mol/cm2] | | | | | |
| 0.25 | 1.13E−08 | 1.63E−08 | 1.18E−08 | 1.31E−08 | 2.72E−09 |
| 0.5 | 4.90E−08 | 6.21E−08 | 4.49E−08 | 5.20E−08 | 8.99E−09 |
| 1 | 1.51E−07 | 1.86E−07 | 1.40E−07 | 1.59E−07 | 2.41E−08 |
| 1.5 | 2.77E−07 | 3.36E−07 | 2.65E−07 | 2.93E−07 | 3.81E−08 |
| 2 | 4.08E−07 | 4.35E−07 | 4.11E−07 | 4.38E−07 | 4.93E−08 |
| 2.5 | 5.19E−07 | 6.38E−07 | 5.50E−07 | 5.69E−07 | 6.17E−08 |
| 3 | 6.84E−07 | 8.06E−07 | 7.01E−07 | 7.30E−07 | 6.62E−08 |
| 4 | 1.03E−06 | 1.16E−06 | 9.99E−07 | 1.06E−06 | 8.46E−08 |
| 5 | 1.37E−06 | 1.48E−06 | 1.30E−06 | 1.38E−06 | 9.24E−08 |
| 6 | 1.67E−06 | 1.77E−06 | 1.54E−06 | 1.66E−06 | 1.14E−07 |
| Flux | | | | | |
| 0.125 | 9.05E−08 | 1.30E−07 | 9.47E−08 | 1.05E−07 | 2.18E−08 |
| 0.375 | 1.51E−07 | 1.83E−07 | 1.32E−07 | 1.56E−07 | 2.59E−08 |
| 0.75 | 2.03E−07 | 2.48E−07 | 1.90E−07 | 2.14E−07 | 3.02E−08 |
| 1.25 | 2.52E−07 | 3.00E−07 | 2.50E−07 | 2.67E−07 | 2.83E−08 |
| 1.75 | 2.64E−07 | 3.18E−07 | 2.92E−07 | 2.91E−07 | 2.72E−08 |
| 2.25 | 2.21E−07 | 2.86E−07 | 2.78E−07 | 2.62E−07 | 3.53E−08 |
| 2.75 | 3.29E−07 | 3.36E−07 | 3.01E−07 | 3.22E−07 | 1.85E−08 |
| 3.5 | 3.44E−07 | 3.52E−07 | 2.98E−07 | 3.31E−07 | 2.88E−08 |
| 4.5 | 3.38E−07 | 3.22E−07 | 2.98E−07 | 3.19E−07 | 2.03E−08 |
| 5.5 | 3.07E−07 | 2.91E−07 | 2.46E−07 | 2.81E−07 | 3.13E−08 |

TABLE 21

| 5 mM | | | | | |
|---|---|---|---|---|---|
| Time[hour] | No. 1 | No. 2 | No. 3 | Mean | S.D. |
| Q[mol/cm2] | | | | | |
| 0.5 | 3.81E−08 | 3.44E−08 | 5.61E−08 | 4.28E−08 | 1.16E−08 |
| 1 | 1.25E−07 | 1.23E−07 | 1.61E−07 | 1.36E−07 | 2.11E−08 |
| 1.5 | 2.32E−07 | 2.38E−07 | 2.89E−07 | 2.53E−07 | 3.16E−08 |
| 2 | 3.53E−07 | 3.72E−07 | 4.34E−07 | 3.86E−07 | 4.25E−08 |
| 2.5 | 4.73E−07 | 5.22E−07 | 5.87E−07 | 5.27E−07 | 5.71E−08 |
| 3 | 6.05E−07 | 6.71E−07 | 7.58E−07 | 6.78E−07 | 7.71E−08 |
| 4 | 8.97E−07 | 9.89E−07 | 1.10E−06 | 9.96E−07 | 1.02E−07 |
| 5 | 1.16E−06 | 1.26E−06 | 1.40E−06 | 1.27E−06 | 1.21E−07 |
| 6 | 1.42E−06 | 1.54E−06 | 1.67E−06 | 1.54E−06 | 1.25E−07 |
| Flux | | | | | |
| 0.25 | 1.52E−07 | 1.38E−07 | 2.24E−07 | 1.71E−07 | 4.64E−08 |
| 0.75 | 1.73E−07 | 1.78E−07 | 2.09E−07 | 1.87E−07 | 1.95E−08 |
| 1.25 | 2.14E−07 | 2.29E−07 | 2.57E−07 | 2.33E−07 | 2.20E−08 |
| 1.75 | 2.43E−07 | 2.68E−07 | 2.90E−07 | 2.67E−07 | 2.35E−08 |
| 2.25 | 2.39E−07 | 3.00E−07 | 3.05E−07 | 2.81E−07 | 3.64E−08 |
| 2.75 | 2.64E−07 | 2.99E−07 | 3.44E−07 | 3.02E−07 | 4.00E−08 |
| 3.5 | 2.92E−07 | 3.19E−07 | 3.43E−07 | 3.18E−07 | 2.53E−08 |
| 4.5 | 2.59E−07 | 2.69E−07 | 2.96E−07 | 2.75E−07 | 1.93E−08 |
| 5.5 | 2.62E−07 | 2.84E−07 | 2.71E−07 | 2.72E−07 | 1.12E−08 |

TABLE 22

| 10 mM | | | | | |
|---|---|---|---|---|---|
| Time[hour] | No. 1 | No. 2 | No. 3 | Mean | S.D. |
| Q[mol/cm2] | | | | | |
| 0.5 | 3.29E−08 | 7.52E−08 | 4.26E−08 | 5.02E−08 | 2.22E−08 |
| 1 | 1.08E−07 | 2.23E−07 | 1.22E−07 | 1.51E−07 | 6.31E−08 |
| 1.5 | 1.96E−07 | 3.94E−07 | 2.17E−07 | 2.69E−07 | 1.08E−07 |
| 2 | 2.90E−07 | 5.59E−07 | 3.12E−07 | 3.87E−07 | 1.49E−07 |
| 2.5 | 4.17E−07 | 7.45E−07 | 4.26E−07 | 5.29E−07 | 1.87E−07 |
| 3 | 5.29E−07 | 9.11E−07 | 5.42E−07 | 6.61E−07 | 2.17E−07 |
| 4 | 7.85E−07 | 1.25E−06 | 7.79E−07 | 9.38E−07 | 2.70E−07 |
| 5 | 1.08E−06 | 1.58E−06 | 1.02E−06 | 1.22E−06 | 3.07E−07 |
| 6 | 1.33E−06 | 1.90E−06 | 1.27E−06 | 1.50E−06 | 3.47E−07 |
| Flux | | | | | |
| 0.25 | 1.32E−07 | 3.01E−07 | 1.71E−07 | 2.01E−07 | 8.86E−08 |
| 0.75 | 1.49E−07 | 2.96E−07 | 1.59E−07 | 2.02E−07 | 8.23E−08 |
| 1.25 | 1.77E−07 | 3.40E−07 | 1.90E−07 | 2.36E−07 | 9.07E−08 |
| 1.75 | 1.89E−07 | 3.31E−07 | 1.89E−07 | 2.36E−07 | 8.19E−08 |
| 2.25 | 2.53E−07 | 3.72E−07 | 2.29E−07 | 2.84E−07 | 7.67E−08 |
| 2.75 | 2.26E−07 | 3.33E−07 | 2.31E−07 | 2.63E−07 | 6.06E−08 |
| 3.5 | 2.56E−07 | 3.38E−07 | 2.38E−07 | 2.77E−07 | 5.35E−08 |
| 4.5 | 2.94E−07 | 3.27E−07 | 2.36E−07 | 2.86E−07 | 4.57E−08 |
| 5.5 | 2.49E−07 | 3.20E−07 | 2.51E−07 | 2.73E−07 | 4.02E−08 |

TABLE 23

| 10 mM 2nd | | | | | |
|---|---|---|---|---|---|
| Time[hour] | no. 4 | no. 5 | no. 6 | Mean | S.D. |
| 0.5 | 4.42E−08 | 5.25E−08 | 6.00E−08 | 5.22E−08 | 7.92E−09 |
| 1 | 1.25E−07 | 1.44E−07 | 1.57E−07 | 1.42E−07 | 1.65E−08 |
| 1.5 | 2.24E−07 | 2.54E−07 | 2.78E−07 | 2.52E−07 | 2.70E−08 |
| 2 | 3.30E−07 | 3.80E−07 | 4.09E−07 | 3.73E−07 | 4.00E−08 |
| 2.5 | 4.42E−07 | 5.10E−07 | 5.44E−07 | 4.99E−07 | 5.23E−08 |
| 3 | 5.59E−07 | 6.48E−07 | 7.11E−07 | 6.39E−07 | 7.64E−08 |
| 4 | 7.92E−07 | 9.45E−07 | 1.03E−06 | 9.21E−07 | 1.19E−07 |
| 5 | 1.03E−06 | 1.20E−06 | 1.32E−06 | 1.18E−06 | 1.46E−07 |
| 6 | 1.30E−06 | 1.48E−06 | 1.63E−06 | 1.47E−06 | 1.62E−07 |
| Flux | | | | | |
| 0.25 | 1.77E−07 | 2.10E−07 | 2.40E−07 | 2.09E−07 | 3.17E−08 |
| 0.75 | 1.61E−07 | 1.84E−07 | 1.95E−07 | 1.80E−07 | 1.72E−08 |

TABLE 23-continued 10 mM 2nd

| Time[hour] | no. 4 | no. 5 | no. 6 | Mean | S.D. |
|---|---|---|---|---|---|
| 1.25 | 1.99E−07 | 2.19E−07 | 2.41E−07 | 2.19E−07 | 2.11E−08 |
| 1.75 | 2.12E−07 | 2.53E−07 | 2.63E−07 | 2.43E−07 | 2.68E−08 |
| 2.25 | 2.23E−07 | 2.59E−07 | 2.70E−07 | 2.51E−07 | 2.46E−08 |
| 2.75 | 2.34E−07 | 2.76E−07 | 3.33E−07 | 2.81E−07 | 4.96E−08 |
| 3.5 | 2.33E−07 | 2.97E−07 | 3.15E−07 | 2.82E−07 | 4.30E−08 |
| 4.5 | 2.40E−07 | 2.50E−07 | 2.97E−07 | 2.63E−07 | 3.02E−08 |
| 5.5 | 2.70E−07 | 2.82E−07 | 3.03E−07 | 2.85E−07 | 1.66E−08 |

TABLE 24

50 mM

| Time[hour] | no. 4 | no. 5 | no. 6 | Mean | S.D. |
|---|---|---|---|---|---|
| 0.25 | 1.85E−08 | 8.22E−09 | 3.08E−08 | 1.92E−08 | 1.13E−08 |
| 0.5 | 5.32E−08 | 2.47E−08 | 8.13E−08 | 5.31E−08 | 2.83E−08 |
| 1 | 1.46E−07 | 8.10E−08 | 2.28E−07 | 1.52E−07 | 7.36E−08 |
| 1.5 | 2.48E−07 | 1.47E−07 | 3.51E−07 | 2.49E−07 | 1.02E−07 |
| 2 | 3.53E−07 | 2.18E−07 | 5.00E−07 | 3.57E−07 | 1.41E−07 |
| 2.5 | 4.65E−07 | 3.00E−07 | 6.48E−07 | 4.71E−07 | 1.74E−07 |
| 3 | 5.65E−07 | 3.87E−07 | 7.75E−07 | 5.76E−07 | 1.94E−07 |
| 4 | 7.84E−07 | 5.78E−07 | 1.05E−06 | 8.04E−07 | 2.37E−07 |
| 5 | 1.01E−06 | 7.84E−07 | 1.31E−06 | 1.04E−06 | 2.65E−07 |
| 6 | 1.21E−06 | 9.84E−07 | 1.51E−06 | 1.24E−06 | 2.6SE−07 |
| Flux | | | | | |
| 0.125 | 1.48E−07 | 6.57E−08 | 2.47E−07 | 1.53E−07 | 9.06E−08 |
| 0.375 | 1.39E−07 | 6.58E−08 | 2.02E−07 | 1.36E−07 | 6.81E−08 |
| 0.75 | 1.86E−07 | 1.13E−07 | 2.93E−07 | 1.97E−07 | 9.09E−08 |
| 1.25 | 2.03E−07 | 1.32E−07 | 2.47E−07 | 1.94E−07 | 5.78E−08 |
| 1.75 | 2.11E−07 | 1.42E−07 | 2.97E−07 | 2.17E−07 | 7.79E−08 |
| 2.25 | 2.24E−07 | 1.64E−07 | 2.96E−07 | 2.28E−07 | 6.62E−08 |
| 2.75 | 2.01E−07 | 1.74E−07 | 2.55E−07 | 2.10E−07 | 4.13E−08 |
| 3.5 | 2.19E−07 | 1.91E−07 | 2.75E−07 | 2.28E−07 | 4.29E−08 |
| 4.5 | 2.27E−07 | 2.06E−07 | 2.61E−07 | 2.31E−07 | 2.76E−08 |
| 5.5 | 1.99E−07 | 2.01E−07 | 2.01E−07 | 2.00E−07 | 1.01E−09 |

TABLE 25

100 mM

| Time[hour] | no. 4 | no. 5 | no. 6 | Mean | S.D. |
|---|---|---|---|---|---|
| 0.5 | 2.04E−08 | 4.21E−08 | 3.31E−08 | 3.19E−08 | 1.09E−08 |
| 1 | 5.74E−08 | 1.18E−07 | 9.01E−08 | 8.86E−08 | 3.04E−08 |
| 1.5 | 1.06E−07 | 2.10E−07 | 1.61E−07 | 1.59E−07 | 5.23E−08 |
| 2 | 1.54E−07 | 2.96E−07 | 2.30E−07 | 2.27E−07 | 7.13E−08 |
| 2.5 | 2.14E−07 | 3.89E−07 | 3.05E−07 | 3.03E−07 | 8.76E−08 |
| 3 | 2.71E−07 | 4.77E−07 | 3.75E−07 | 3.75E−07 | 1.03E−07 |
| 4 | 4.11E−07 | 6.61E−07 | 5.46E−07 | 5.39E−07 | 1.25E−07 |
| 5 | 5.61E−07 | 8.42E−07 | 7.14E−07 | 7.06E−07 | 1.41E−07 |
| 6 | 7.16E−07 | 1.01E−06 | 8.86E−07 | 8.70E−07 | 1.46E−07 |
| Flux | | | | | |
| 0.25 | 8.17E−08 | 1.68E−07 | 1.33E−07 | 1.27E−07 | 4.35E−08 |
| 0.75 | 7.40E−08 | 1.52E−07 | 1.14E−07 | 1.13E−07 | 3.92E−08 |
| 1.25 | 9.67E−08 | 1.84E−07 | 1.43E−07 | 1.41E−07 | 4.38E−08 |
| 1.75 | 9.56E−08 | 1.71E−07 | 1.38E−07 | 1.35E−07 | 3.79E−08 |
| 2.25 | 1.21E−07 | 1.87E−07 | 1.49E−07 | 1.52E−07 | 3.29E−08 |
| 2.75 | 1.14E−07 | 1.76E−07 | 1.41E−07 | 1.44E−07 | 3.09E−08 |
| 3.5 | 1.40E−07 | 1.84E−07 | 1.70E−07 | 1.65E−07 | 2.25E−08 |
| 4.5 | 1.50E−07 | 1.81E−07 | 1.68E−07 | 1.66E−07 | 1.56E−08 |
| 5.5 | 1.55E−07 | 1.66E−07 | 1.72E−07 | 1.64E−07 | 8.70E−09 |

As a result of these, it is recognized that if the concentration of the salt is high, the cumulative permeated amount is slightly reduced. It is thought that this is because the permeability of the drug is prevented by increasing the concentration of the competing ion. In the case of the lower concentration of the salt such as about 1 to 10 mM, it was revealed that these influence is small. Moreover, although there are very few differences at a later stage of the experiment regarding the time courses flux of a cumulative amount permeated profile, however, it is thought that it is came under the influence of the competing ion at a first stage, and the lower concentration of the salt (1 mM) shows almost the same behavior as water.

Accordingly, it is recognized that the lower concentration of the salt of phosphoric acid is desired, in particular, about 0 mM to 10 mM makes it possible to give no influence to the permeability and improve the stability of the chemical drug (the stability is examined at only 1 mM. It is still stable after 18 months).

INDUSTRIAL APPLICABILITY

The present inventions relate to the drug product for administering the bioactive material from a transdermal or transmucosal route using the electric energy, and make mainly a contribution in the fields of the medical treatment.

The invention claimed is:

1. A pharmaceutical composition for iontophoresis wherein the composition contains a nonionic synthetic polymer, betamethasone sodium phosphate, solvent and ethylenediamine tetraacedic acid (EDTA), wherein the mixing amount of ethylenediamine tetraacetic acid (EDTA) is 0.05 to 0.15 percent by weight, and the solvent is a phosphate buffer solution wherein the concentration of phosphate buffer solution is 1 to 10 mM.

2. A pharmaceutical composition for iontophoresis according to claim 1, wherein the nonionic synthetic polymer is polyvinyl alcohol (PVA).

3. A pharmaceutical composition for iontophoresis according to claim 1, wherein the mixing amount of the polyvinyl alcohol (PVA) is 0.5 to 30.0 percent by weight.

4. A pharmaceutical composition for iontophoresis according to claim 3, wherein the mixing amount of the polyvinyl alcohol (PVA) is less or equal to 20 percent by weight.

5. A pharmaceutical composition for iontophoresis according to claim 1, wherein the amount of betamethasone sodium phosphate is 1 to 12 percent by weight.

6. A pharmaceutical composition for iontophoresis according to claim 5, wherein the amount of betamethasone sodium phosphate is 1 to 4 percent by weight.

7. A pharmaceutical composition for iontophoresis according to claim 1, wherein the pH on the surface of the composition is in the range of 7 to 8.

8. A drug product for iontophoresis comprising the composition according to claim 1, and an adhesive layer.

9. A drug product for iontophoresis according to claim 1, wherein the adhesive layer comprises at least one selected from the group consisting of an acrylic system, a silicon system, a synthetic rubber system and a natural rubber system.

10. An iontophoresis administration method, wherein betamethasone sodium phosphate is administered by using the pharmaceutical composition according to claim 1.

11. An iontophoresis administration method according to claim 10, wherein betamethasone sodium phosphate is transferred to an arthrosis through a percutaneous route by going through a perimysia from a supporting layer, and being zonally distributed to the inner side of a perimysia and a synovial membrane.

12. A method of treatment for at least one noninfectious disorder selected from the group consisting of rheumatoid arthritis, arthrosis deformans, tendinitis, tendovaginitis, and peritendinitis by administering betamethasone sodium phosphate according to the iontophoresis administration method of claim 10.

* * * * *